(12) United States Patent
Jung et al.

(10) Patent No.: US 11,547,737 B2
(45) Date of Patent: Jan. 10, 2023

(54) COMPOSITIONS AND METHODS FOR TREATING VIRUS INFECTION

(71) Applicant: NovMetaPharma Co., Ltd., Seoul (KR)

(72) Inventors: Hoe-Yune Jung, Pohang-si (KR); Heonjong Lee, Incheon (KR); Dohyun Lee, Pohang-si (KR)

(73) Assignee: NovMetaPharma Co., Ltd., Seoul (KR)

( * ) Notice: Subject to any disclaimer, the term of this patent is extended or adjusted under 35 U.S.C. 154(b) by 0 days.

(21) Appl. No.: 17/350,170

(22) Filed: Jun. 17, 2021

(65) Prior Publication Data

US 2021/0393731 A1 Dec. 23, 2021

Related U.S. Application Data

(60) Provisional application No. 63/040,302, filed on Jun. 17, 2020.

(51) Int. Cl.
  *A61K 38/05* (2006.01)
  *A61K 31/685* (2006.01)
  *A61K 31/56* (2006.01)
  *A61K 31/315* (2006.01)

(52) U.S. Cl.
  CPC ............ *A61K 38/05* (2013.01); *A61K 31/315* (2013.01); *A61K 31/56* (2013.01); *A61K 31/685* (2013.01)

(58) Field of Classification Search
  None
  See application file for complete search history.

(56) References Cited

U.S. PATENT DOCUMENTS

| 5,834,032 A | 11/1998 | Song |
| 2009/0004291 A1 | 1/2009 | Song et al. |
| 2019/0290720 A1* | 9/2019 | Jung ...................... A61P 31/00 |

FOREIGN PATENT DOCUMENTS

WO  2019078663 A2  4/2019

OTHER PUBLICATIONS

Dolgin "Stocking the Shelves for the Next Pandemic," Nature, 2021, vol. 592, pp. 340-343 (Year: 2021).*
Andrei "Vaccines and Antivirals: Grand Challenges and Great Opportunities," Frontiers in Virology, 2021, vol. 1, Artyicle 666548, pp. 1-8 (Year: 2021).*
Alba Minelli et al., "Cyclo(His-Pro) exerts anti-inflammatory effects by modulating NF-κB and Nrf2 signalling", The International Journal of Biochemistry & Cell Biology, vol. 44, 2012, pp. 525-535, (11 pages total).
A. Minelli et al., "Focus on cyclo(His-Pro): history and perspectives as antioxidant peptide", Amino Acids, vol. 35, 2008, pp. 283-289 (7 pages total).
Written Opinion of the International Searching Authority dated Sep. 15, 2021, in International Application No. PCT/IB2021/055375.
International Search Report dated Sep. 15, 2021, in International Application No. PCT/IB2021/055375.

* cited by examiner

*Primary Examiner* — Christina Bradley
(74) *Attorney, Agent, or Firm* — Sughrue Mion, PLLC

(57) ABSTRACT

Compositions and methods for treating viral infection are disclosed. The compositions contain a combination of zinc and a cyclo(His-Pro), in effective amounts. The composition containing a combination of zinc and a cyclo(His-Pro) can be used to treat viral infections including SARS-CoV-2 infections in mammals.

20 Claims, 14 Drawing Sheets

COMPOSITIONS AND METHODS FOR TREATING VIRUS INFECTION

CROSS REFERENCE TO RELATED APPLICATIONS

This application claims priority to U.S. provisional Application No. 63/040,302 filed Jun. 17, 2020, of which content is incorporated by reference herein in its entirety.

TECHNICAL FIELD

The present disclosure is directed to a composition effective in inhibiting replication of retrovirus or RNA virus. The present disclosure also is directed to a method for treating viral infections using the composition.

BACKGROUND

Positive-stranded RNA (+RNA) viruses include major pathogens of humans and livestock, such as severe acute respiratory syndrome coronavirus (SARS-CoV), other human coronaviruses, the arteriviruses equine arteritis virus (EAV), and porcine reproductive and respiratory syndrome virus (PRRSV). Despite a variety of replication strategies, these viruses are common in that an RNA-dependent RNA polymerase functions as the core enzyme of their RNA-synthesizing machinery. Viral RNA replication is a process fundamental to viral pathogenicity and requires specific recognition of RNA features by proteins. RNA-dependent RNA polymerase is a complex composed of viral and cellular proteins that directs viral RNA synthesis from infecting RNA templates. The RNA-dependent RNA polymerase is commonly embedded in a membrane-associated replication complex that is assembled from viral RNA, and viral and host proteins. Given their crucial function in the viral replicative cycle, RNA-dependent RNA polymerase are key targets for antiviral research.

Coronaviruses are large, enveloped, positive-stranded RNA viruses. They cause the common cold in all age groups accounting for approximately 15% of all colds. Coronaviruses have been implicated in the etiology of gastrointestinal disease in infants. They also cause economically important diseases in animals (e.g. avian infectious bronchitis and porcine transmissible gastroenteritis). Coronaviruses get their name because in electron micrographs the envelope glycoproteins appear to form a halo or corona around the periphery of the virion.

Coronaviruses are a major cause of common colds in the winter months. The virus is found throughout the world. Antibodies begin to appear in childhood, and are found in more than 90% of adults. The frequency of coronavirus respiratory infections is highly variable from year to year. The highest incidence occurs in years when rhinovirus colds are lowest. Coronavirus colds tend to occur in defined outbreaks.

Coronaviruses are transmitted by aerosols of respiratory secretions, by the fecal-oral route, and by mechanical transmission. Most virus growth occurs in epithelial cells. Occasionally the liver, kidneys, heart or eyes may be infected, as well as other cell types such as macrophages. In cold-type respiratory infections, growth appears to be localized to the epithelium of the upper respiratory tract, but there is currently no adequate animal model for the human respiratory coronaviruses.

In late 2002, several hundred cases of an atypical pneumonia were reported in Guangdong Province of the People's Republic of China. Months later, similar cases were identified in Canada, Vietnam and Hong Kong. The World Health Organization (WHO) identified the emergent disease as "severe acute respiratory syndrome" or SARS. In March 2003, a novel coronavirus (SARS-CoV) was discovered in association with cases of SARS.

In 2012, middle-east respiratory syndrome coronavirus (MERS-CoV) emerged in the Arabian Peninsula, where it remains a major public health concern. A previously unknown coronavirus, named SARS-CoV-2, was discovered in December 2019 in Wuhan, Hubei province of China and was sequenced and isolated by January 2020. SARS-CoV-2 is associated with an outbreak of atypical pneumonia (COVID-19) that has affected over 175 million people and caused about 3.8 million deaths worldwide, according to World Heath Organization (WHO).

Both SARS-CoV and SARS-CoV-2 are closely related and originated in bats, who most likely serve as reservoir host for these two viruses.

The complete genome of SARS-CoV has been identified, as well as common variants thereof The genome of SARS-CoV is a 29,727-nucleotide polyadenylated RNA, has 11 open reading frames, and 41% of the residues are G or C. The genomic organization is typical of coronaviruses, with the characteristic gene order (5'-replicase (rep), spike (S), envelope (E), membrane (M), nucleocapsid (N)-3' and short untranslated regions at both termini. The SARS-CoV rep gene, which comprises about two-thirds of the genome, is predicted to encode two polyproteins that undergo co-translational proteolytic processing. There are four open reading frames (ORFs) downstream of rep that are predicted to encode the structural proteins, S, E, M and N, which are common to all known coronaviruses.

Coronaviruses have the largest genomes of all RNA viruses and replicate by a unique mechanism which results in a high frequency of recombination. Virions mature by budding at intracellular membranes, and infection with some coronaviruses induces cell fusion.

As with most RNA viruses, coronavirus replication takes place in the cytoplasm. Once the viral RNA enters the cytoplasm it is translated to produce the viral RNA-dependent RNA polymerase which then makes a full-length complementary (minus strand) copy of the virion RNA. The minus strand serves a template for transcription of the seven capped and polyadenylated mRNAs. These are arranged as a nested set in which all have the same 3' end but each is smaller by one gene than the next larger one. All have the same 5' end, a leader sequence, encoded only at the 5' end of the genome RNA. This suggests each mRNA is transcribed by a mechanism in which transcription starts by synthesizing the leader sequence and then skips to the beginning of one of the genes with each mRNA ending at the same 3' end.

The multi-subunit CoV RNA synthesis machinery is a complex of non-structural proteins (nsp) produced as cleavage products of the ORF1a and ORF1ab viral polyproteins. Kirchdoerfer and Ward (Nature Communications, 10, Article number: 2342 (2019), published May 28, 2019) reported a crystalline structure of SARS-CoV nsp12 polymerase bound to co-factors, nsp7 and nsp8. Kirchdoerfer and Ward reported that the nsp12 RNA-dependent RNA polymerase possesses an architecture common to all viral polymerases as well as a large N-terminal extension containing a kinase-like fold.

Velthuis et al. reported that using an activity assay for replication and transcription complexes (RTCs) isolated from cells infected with SARS-CoV and equine arteritis virus (EAV), $Zn^{2+}$ efficiently inhibits in vitro the RNA-synthesizing activity of the RTCs of both viruses.

As of May 2021, the U.S. Food and Drug Administration (FDA) has approved three COVID-19 vaccines under the emergency use authorization (EUA) and approved one drug, remdesivir (Veklury) to treat COVID-19, in the US. In July 2020, WHO discontinued the trial using hydroxychloroquine and lopinavir/ritonavir for hospitalized patients because the interim trial results showed that hydroxychloroquine and lopinavir/ritonavir produced little or no reduction in the mortality of hospitalized COVID-19 patients when compared to standard of care.

Potential antiviral drugs are usually subjected to an intensive and costly screening program to determine whether the drug can preferentially inhibit a viral process. One such drug is Aziduovir, which is utilized more readily by the reverse transcriptase of the human immunodeficiency virus (HIV) than by host cellular polymerases. Yet other potential antiviral therapies, including antisense molecules and ribozymes, are difficult to produce due to the need for complex molecular recombinant technology.

Thus, there is a continuing need for agents that specifically inhibit viral replication. And there is ongoing needs for agents that can treat coronavirus infections in animals. In embodiments, the coronavirus may be SARS-CoV-1, MERS-CoV, SARS-CoV-2, and the like.

Zinc ions are known to be involved in many different cellular processes and have proven crucial for the proper folding and activity of various cellular enzymes and transcription factors. In cell culture studies, high $Zn^{2+}$ concentrations and the addition of compounds that stimulate cellular import of $Zn^{2+}$ such as hinokitol (HK), pyrrolidine dithiocarbamate (PDTC) and pyrithione (PT), were found to inhibit the replication of various RNA viruses, including influenza virus, respiratory syncytial virus and several picornaviruses. The intracellular concentration of free $Zn^{2+}$ is maintained at a relatively low level by metallothioneins, likely due to the fact that $Zn^{2+}$ can serve as intracellular second messenger and may trigger apoptosis or a decrease in protein synthesis at elevated concentrations.

Cyclo(-His-Pro) (cyclo-Hirpro or CHP), $C_{11}H_{14}N_4O_2$, has been known as an anhydrous dipeptide having the CAS Registry Number 53109-32-3. It is an endogenous cyclic dipeptide derived in vivo from the hydrolytic removal of the amino-terminal pyroglutamic acid residue of the hypothalamic thyrotropin-releasing hormone.

Rosenthal et al. (Life Sciences 70 (2001), 337-348) reported that cyclo(-His-Pro) enhanced zinc absorption and uptake by muscle tissues and by intestinal segments.

U.S. Pat. No. 5,834,032 describes the use of cyclo(His-Pro) and zinc to lower insulin levels as a method for treating insulin-resistant diabetes. The content of U.S. Pat. No. 5,834,032 is incorporated by reference herein in its entirety.

U.S. Pat. No. 10,058,520 discloses the use of thyroid hormone, cyclo(His-Pro) and a zinc salt together in treating or delaying the onset of Alzheimer's disease and/or dementia in mammals. The content of U.S. Pat. No. 10,058,520 is incorporated by reference herein in its entirety.

Known cyclo(-His-Pro) that has been reported in literature and has potential therapeutic applications, is of crystalline anhydrous form. However, certain anhydrous forms may be unstable. Possible disadvantages of using Pattern 1 include: (1) apparent physical instability at ambient to high humidity conditions; and (2) potential chemical instability due to water activity resulting in the formation of diastereomers of the desired L,L-dipeptides such as D,L-CHP, L,D-CHP, or D,D-CHP.

SUMMARY

The present disclosure provides a method for treating an RNA viral infection by administering a composition comprising cyclo(-His-Pro) ("CHP") and zinc.

In an embodiment, the method of treating RNA viral infection in subject in need thereof comprises administering an effective amount of a pharmaceutical composition comprising a CHP and zinc, as active ingredients, to the mammal. In some embodiments, the composition, employed in the methods described herein, consists essentially of a CHP and zinc, as active ingredients. In some embodiments, the composition, employed in the methods described herein, consists of a CHP and zinc, as active ingredients, and one or more pharmaceutically acceptable excipients known in the art. In some embodiments, the methods described herein, may essentially consist of administering a CHP and zinc, administering a CHP, zinc and an additional anti-viral agent, administering a CHP, zinc, a steroid, or administering a CHP, zinc, a steroid, and an additional anti-viral agent. In embodiments, a CHP, zinc, a steroid, and/or an additional anti-viral agents may be administered simultaneously or sequentially in any order.

According to an embodiment, the RNA virial infection is an infection by MERS virus, SARS-CoV-1, SARS-CoV-2 (COVID-19), Ebola virus, influenza virus, measles virus, and HIV-1 (human immunodeficiency virus type 1). In a particular embodiment, the virus infection is SARS-CoV-2 (COVID-19) infection.

According embodiments of the methods and compositions described herein, the cylco(-His-Pro) or CHP is anhydrous form, or a crystalline cyclo(-His-Pro) hydrate ("CHP hydrate") as described in U.S. Application Publication no. 2020-0017509A and co-pending application Ser. No. 16/901,676, of which the entire contents are incorporated herein by reference, or a mixture of anhydrous form and the CHP hydrate. In embodiments, the composition may comprise anhydrous CHP converted from the CHP hydrate during pharmaceutical formulation process.

In an embodiment, the CHP hydrate may comprise peaks in 2θ values of about 13.5°-about 13.9°, about 16.8°-about 17.2°, and about 27.1°-about 27.5°.

In another embodiment, the CHP hydrate may comprise three or more peaks in 2θ values selected from about 9.8°-about 10.2°, about 13.5°-about 13.9°, about 16.8°-about 17.2°, about 17.9°-about 18.3°, about 20.0°-about 20.2°, and about 27.1°-about 27.5°.

In an embodiment, the CHP hydrate is stable at typical room temperature storage conditions for about 6 months, or about 12 months, or about 18 months, or about 24 months, or about 36 months.

In another embodiment, the CHP hydrate is substantially pure. In some embodiments, the CHP hydrate material is at least about 90% pure, or at least about 95%, 96%, 97%, 98%, 99%, or 100% pure.

In another embodiment, the CHP hydrate material may be characterized by at least two of the following:
(a) an X-ray powder diffractogram comprising at least two peaks in 2θ values chosen from the following list: about 9.8°-about 10.2°, about 13.5°-about 13.9°, about 16.8°-about 17.2°, about 17.9°-about 18.3°, about 20.0°-about 20.2°, and about 27.1°-about 27.5°;
(b) pKa of about 6.4;
(c) birefringent with a fragmented, rod-like morphology when analyzed by polarized light microscopy;

(d) an initial weight loss of about 6.5% (0.9 equivalent of water), followed by sample degradation at about 280° C. when analyzed by thermogravimetric analysis technique;

(e) an endotherm with an onset of about 99° C. and a peak at about 102° C. in the first heat cycle of DSC;

(f) start of dehydration below about 10% relative humidity (RH), loss of about 5.8 wt % from 10 to 0% RH (0.8 equivalent of water) and hydration from 0 to about 40% RH in the 40° C. dynamic vapor sorption analysis;

(g) start of dehydration below about 20% RH, loss of about 6.1 wt % from about 20 to 0% RH (0.8 equivalent of water) and rehydration from 0 to about 40% RH in the 50° C. dynamic vapor sorption analysis; and (h) start of dehydration below about 20% RH, loss of about 7 wt % from about 20 to 0% RH (1.0 equivalent of water), and rehydration from 0 to about 40% RH in the 60° C. dynamic vapor sorption analysis.

In an embodiment, zinc may be zinc metal, an organic or inorganic salt of zinc, zinc oxide, zinc hydroxide, or a zinc ion. Organic zinc may include, is not limited to, zinc chloride, zinc acetate, zinc gluconate, zinc stearate, zinc sulfate, zinc picolinate, zinc orotate, or zinc citrate.

In one embodiment, a method of treating the RNA viral infection includes administering a pharmaceutically effective amount of zinc and an effective amount of CHP. In certain embodiments, the zinc and the CHP are administered in the same composition. In other embodiments, the zinc salt and the CHP are administered in different compositions.

In the above embodiment, the zinc salt and the CHP may be administered in varying amounts. In some embodiments, the weight ratio of zinc to CHP is from about 1:100 to about 100:1. In some embodiments, the weight ratio of zinc to CHP is from about 1:10 to about 100:1. In some embodiments, the weight ratio of zinc to CHP is from about 1:6 to about 5:1. In some embodiments, the weight ratio of zinc to CHP is from about 1:15 to about 20:1. In some embodiments, the weight ratio of zinc to CHP is from about 1:30 to about 4:1. In some embodiments, the weight ratio of zinc to CHP is from about 1:8 to about 4:1. In some embodiments, the weight ratio of zinc to CHP is from about 1:40 to about 40:1. The weight ratio is based on the amount of zinc as calculated as cation and of the amount of CHP, as calculated as anhydrous CHP. Therefore, when CHP monohydrate is employed or a mixture of anhydrous CHP and CHP hydrate is employed, as an active ingredient, the amount of CHP monohydrate or the mixture in the composition may be determined accordingly.

In certain embodiments, the zinc and CHP are administered to the mammal in an amount that causes a decrease in a serum level of amyloid beta protein. In certain embodiments, the serum level is decreased in an amount ranging between 0.001% to about 0.5%. In certain embodiments, the serum level is decreased in an amount ranging between 0.01% to about 1%. In certain embodiments, the serum level is decreased in an amount ranging between 0.1% to about 5%. In certain embodiments, the serum level is decreased in an amount ranging between 1% to about 10%. In certain embodiments, the serum level is decreased in an amount ranging between 1% to about 50%.

In certain embodiments, the zinc is administered to the mammal in an amount from about 0.01 to about 4 mg/kg/day (as calculated as zinc cation). In one embodiment, zinc is administered mammal in an amount from about 0.01 to about 1.5 mg/kg/day. In another embodiment, zinc is administered to the mammal in an amount from about 0.01 to about 0.4 mg/kg/day. In another embodiment, zinc is administered to the mammal in an amount from about 0.1 to about 2 mg/kg/day. In another embodiment, zinc is administered to the mammal in an amount from about 2 to about 4 mg/kg/day. In another embodiment, zinc is administered to the mammal in an amount from about 1 to about 10 mg/kg/day. In another embodiment, zinc is administered to the mammal in an amount from about 3 to about 8 mg/kg/day. In another embodiment, zinc is administered to the mammal in an amount from about 4 to about 7 mg/kg/day. In another embodiment, zinc is administered to the mammal in an amount from about 7 to about 10 mg/kg/day. In another embodiment, zinc is administered to the mammal in an amount from about 0.01 to about 0.1.8 mg/kg/day. In another embodiment, zinc is administered to the mammal in an amount from about 1 to about 1.5 mg/kg/day.

In any of the above mentioned embodiments, CRP may be administered to the mammal in an amount from about 0.007 to about 1.4 mg/kg/day. In some embodiments, CHP is administered to the mammal in an amount from about 0.01 to about 5 mg/kg/day. In some embodiments, CHP is administered to the mammal in an amount from about 0.01 to about 2 mg/kg/day. In some embodiments, CHP is administered to the mammal in an amount from about 2 to about 7 mg/kg/day. In some embodiments, CHP is administered to the mammal in an amount from about 3 to about 5 mg/kg/day. In some embodiments, CHP is administered to the mammal in an amount from about 7 to about 10 mg/kg/day. In some embodiments, CHP is administered to the mammal in an amount from about 0.5 to about 2 mg/kg/day. In some embodiments, CHP is administered to the mammal in an amount from about 0.2 to about 4 mg/kg/day. In some embodiments, CHP is administered to the mammal in an amount from about 0.8 to about 3 mg/kg/day. In some embodiments, CHP is administered to the mammal in an amount from about 1 to about 6 mg/kg/day.

In any of the above mentioned embodiments, CHP may be administered to the mammal in an amount from about 7 mg/kg/day to about 1400 mg/kg/day. In some embodiments, CHP is administered to the mammal in an amount from about 500 mg/kg/day to about 5000 mg/kg/day. In some embodiments, CHP is administered to the mammal in an amount from about 100 to about 2000 mg/kg/day. In some embodiments, CHP or CHP hydrate is administered to the mammal in an amount from about 200 mg/kg/day to about 1000 mg/kg/day. In embodiments, a dose of CHP or CHP hydrate may be about 0.1 mg/kg/day to about 100 mg/kg/day, about 1 mg/kg/day to about 100 mg/kg/day, about 5 mg/kg/day to about 200 mg/kg/day, about 4 mg/kg/day to about 500 mg/kg/day, about 2 mg/kg/day to about 300 g/kg/day, about 2 mg/kg/day to about 40 mg/kg/day, about 3 mg/kg/day to about 35 mg/kg/day, about 4 mg/kg/day to about 100 g/kg/day, about 4 mg/kg/day to about 50 mg/kg/day, about 5 mg/kg/day to about 150 mg/kg/day, about 6 mg/kg/day to about 350 mg/kg/day, about 7 mg/kg/day to about 170 mg/kg/day, about 50 mg/kg/day to about 350 mg/kg/day, 150 mg/kg/day to about 240 mg/kg/day, about 150 mg/kg/day to about 1200 mg/kg/day, about 1 mg/kg/day to about 50 mg/kg/day, about 200 mg/kg/day to about 800 mg/kg/day, about 250 mg/kg/day to about 1200 mg/kg/day, about 20 mg/kg/day to about 240 mg/kg/day, about 6 mg/kg/day to about 180 mg/kg/day, or about 300 mg/kg/day to about 500 mg/kg/day.

In any one of the above mentioned embodiments, one or more therapeutically effective doses of CHP or CHP hydrate are administered per day for a treatment period of at least about 5 days to about one or more months. In any of the above mentioned embodiments, the total dose of CHP or CHP hydrate per day may be independently selected from about 1 to 180 mg, about 1 mg to about 120 mg, about 5 mg to about 100 mg, about 10 mg to about 80 mg, about 10 mg to about 75 mg, about 15 mg to about 120 mg, about 15 mg to about 100 mg, about 15 mg to about 80 mg, about 30 mg to about 120 mg, about 30 mg to about 100 mg, about 30 micro to about 90 mg, about 40 mg to about 70 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 100 mg to about 350 mg, about 10 mg to about 1000 mg, about 12 mg to about 300 mg, about 12 mg to about 120 mg, about 0.01 mg to about 100 mg, about 0.1 mg to about 100 mg, about 0.5 mg to about 100 mg, about 1 mg to about 80 mg, about 1.5 mg to about 60 mg, about 1.8 mg to about 60 mg, and about 1.8 mg to about 40 mg.

In an embodiment, the term "zinc" include, but not limited to, zinc chloride, zinc stearate, zinc acetate, zinc gluconate, zinc carbonate, zinc hydroxides, zinc orotate, zinc citrate, zinc oxide, zinc picolinate.

In any of the above-mentioned embodiments, the composition may consist essentially of CHP and optionally zinc, as an active ingredient (ingredients) for the purpose of treating viral infection in a subject.

BRIEF DESCRIPTION OF THE DRAWINGS

The foregoing features of embodiments will be more readily understood by reference to the following detailed description, taken with reference to the accompanying drawings, in which:

FIG. 6 is an XRPD analysis of CHP hydrate (Pattern 2) hat was returned to the oven, in which the temperature was increased to 50° C. The vial was placed inside the oven for an additional 18 hours. In other words, the bottom graph in FIG. 6 is an XRPD analysis of the product after storing CHP hydrate (Pattern 2) for 18 hour at 80° C., showing mostly Pattern 1 with some Pattern 2 mixed in.

FIG. 7 is an XRPD analysis of CHP hydrate (Pattern 2) that was stored in a vacuum oven for a total of 90 minutes. In other words, the bottom graph in FIG. 7 is an XRPD analysis of the product after storing CHP hydrate (Pattern 2) for 1.5 hour at 50° C. under vacuum, showing mostly Pattern 2 with some Pattern 1 mixed in.

DETAILED DESCRIPTION

Figure 1:
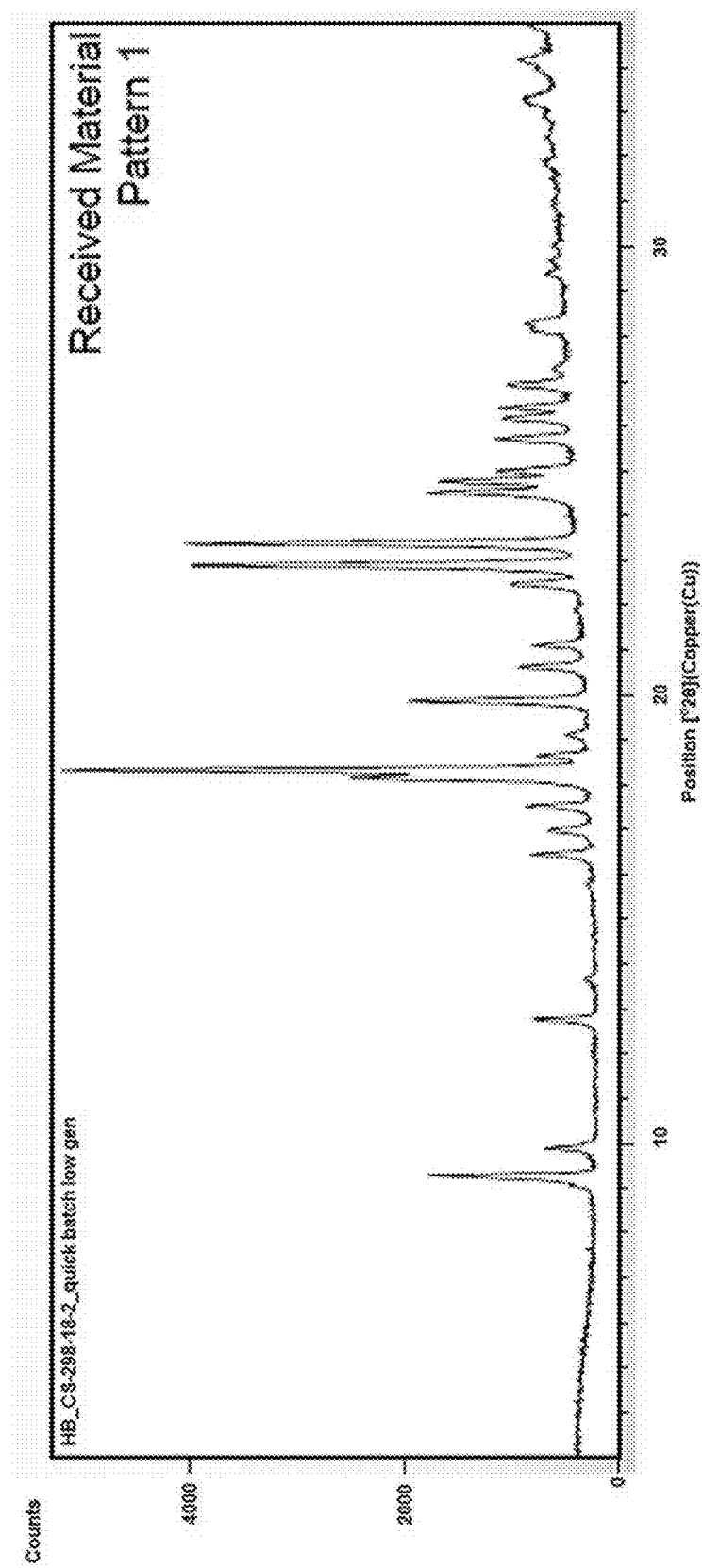
FIG. 1 is X-ray powder diffractogram of anhydrous CHP ("Pattern 1").

The various aspects and embodiments will now be fully described herein. These aspects and embodiments may, however, be embodied in many different forms and should not be construed as limiting; rather, these embodiments are provided so the disclosure will be thorough and complete, and will fully convey the scope of the present subject matter to those skilled in the art. All publications, patents and patent applications cited herein, whether supra or infra, are hereby incorporated by reference in their entirety.

Definitions

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described.

Unless otherwise stated, the use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Consequently, recitation of ranges of values herein are merely intended to serve as a shorthand method of referring individually to each separate value falling within the range, and each separate value is incorporated into the specification as if it were individually recited herein.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection.

The term "active agent" or "drug," as used herein, refers to any chemical that elicits a biochemical response when administered to a human or an animal. The drug may act as a substrate or product of a biochemical reaction, or the drug may interact with a cell receptor and elicit a physiological response, or the drug may bind with and block a receptor from eliciting a physiological response.

The term "treating," as used herein, unless otherwise indicated, means reversing, alleviating, inhibiting the progress of, or preventing the disorder or condition to which such term applies, or one or more symptoms of such disorder or condition. The term "treatment" as used herein, refers to the act of treating, as "treating" is defined immediately above.

The term "therapeutically effective amount" or "effective amount," or "effective dose," as used herein, is the amount of the CHP or CHP hydrate (as calculated as anhydrous CHP) and zinc (as zinc cation) present in a composition described herein that is needed to provide a desired level of drug in the secretions and tissues of the airways and lungs, or alternatively, in the bloodstream of a subject to be treated to give an anticipated physiological response or desired biological effect when such a composition is administered by the chosen route of administration. The precise amount will depend upon numerous factors, for example the specific activity of the composition, the delivery device employed, the physical characteristics of the composition, its intended use, as well as patient considerations such as severity of the disease state, patient cooperation, etc., and can be determined by one skilled in the art based upon the information provided herein.

The term "bioequivalent," as used herein, refers to two compositions, products or methods where the 90% Confidence Intervals (CI) for AUC, partial AUC and/or Cmax are between 0.80 to 1.25.

In some embodiments, the term "substantially as shown in" when referring to an X-ray powder diffraction pattern or a differential scanning calorimetry pattern means that a pattern that is not necessarily identical to those depicted herein, but that falls within the limits of experimental error or deviations, when considered by one of ordinary skill in the art.

DETAILED DESCRIPTION OF THE PREFERRED EMBODIMENT

Anhydrous amorphous cyclo-Hispro (CHP) is illustrated below:

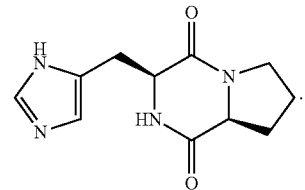 [SMILES: O=C1N[C@@H](Cc2cnc[nH]2)C(=O)N2CCC[C@@H]12]

The CHP monohydrate (or Pattern 2) is illustrated below:

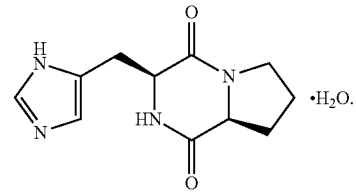 [SMILES: O=C1N[C@@H](Cc2cnc[nH]2)C(=O)N2CCC[C@@H]12]

In one embodiment, the CHP or CHP hydrate is substantially pure.

In an embodiment, the CHP hydrate is characterized by an XRPD diffractogram comprising peaks at about 17±0.2° and about 27.3±0.2° in 2θ.

One embodiment of substantially pure CHP hydrate is characterized by an X-ray powder diffractogram comprising at least three peaks chosen from the following list: 13.7, 17, 18.1, 20.2 and 27.3 degrees (±0.2° in 2θ). Another embodiment is characterized by an XRPD diffractogram comprising at least two peaks chosen from the following list: 10, 13.7, 17, 18.1, 20.2 and 27.3 degrees (±0.2° in 2θ).

In an embodiment, the RNA virus may include arenavirus, coronavirus, filovirus, orthomyxovirus, paramyxovirus, and retrovirus families of viruses. The virus is selected from the group consisting of: Lassa virus, MERS virus, SARS-CoV, SARS-CoV-2, Ebola virus, influenza virus, measles virus, and HIV-1 (human immunodeficiency virus type 1). In an embodiment, the virus is SARS-CoV-2.

The method of administering a composition of zinc and CHP/CHP hydrate may be accomplished by any means. In some embodiments, it is accomplished by ingestion of a tablet, hard or soft capsules, powder, pill, drink, or lozenges. The formation of suitable oral dosage forms, may include, but are not limited to, those that are known to those having skill in the art.

Compositions intended for oral use may be prepared according to any method, and such compositions may contain one or more agents such as sweetening agents, flavoring agents, coloring agents, and/or preserving agents in order to provide pharmaceutically elegant and palatable preparations. Suitable excipients for tablets and capsules include inert diluents, such as safflower oil, lecithin, inositol, soybean shortening oil, gelatin, acacia, glycerin, titanium oxide and soybean oil. The coating of the capsules can be gelatin or a soluble polymer, as is well understood in the art. The tablets or capsules are suitable for oral administration according to a daily administration regimen.

In addition, the methods may also include administering the composition in single or multiple doses. Some embodiments also include administrating the ingredients of the composition in a stepwise manner, or in a manner in which one or more of the ingredients are mixed and administered prior to the administration of the other ingredients.

CHP synthesized from different biochemical sources, including histidine-proline-rich glycoprotein. High levels of CHP are present in many food sources, and are readily absorbed in the gut without chemical or enzymatic destruction.

CHP hydrate can be made by a process described in U.S. application Ser. No. 16/448,083, of which content is incorporated herein by reference, in its entirety.

CHP can be used as a substantially pure form of CHP in amorphous or crystalline form or a substantially pure form of CHP hydrate crystalline, or a mixture of CHP and CHP hydrate, as described in U.S. application Ser. No. 16/448,083, of which the entire content is incorporated herein by reference. The term "CHP/CHP hydrate" as used herein is meant to encompass CHP, CHP hydrate, a crystalline CHP hydrate (Pattern I, Pattern II, and a mixture thereof), and a mixture thereof. And, the term "CHP" and "cyclo-Hispro" and "CHP/CHP hydrate" are interchangeably used to identify the CHP, CHP hydrate, a crystalline CHP hydrate (Pattern I, Pattern II, and a mixture thereof), and a mixture thereof, unless a specific form of CHP is intended by a specific reference to a certain form. In another embodiment, CHP is a crystalline CHP hydrate. In an embodiment, CHP hydrates a CHP monohydrate.

In an embodiment, the zinc and the CHP/CHP hydrate may be administered in varying amounts. In some embodiments, the weight ratio of zinc to CHP/CHP hydrate is from about 1:1000 to about 100:1. In some embodiments, the weight ratio of zinc to CHP/CHP hydrate is from about 1:500 to about 100:1. In some embodiments, the weight ratio of zinc to CHP/CHP hydrate is from about 1:300 to about 100:1. In some embodiments, the weight ratio of zinc to CHP/CHP hydrate is from about 1:200 to about 100:1. In some embodiments, the weight ratio of zinc to CHP/CHP hydrate is 1:100 to about 100:1. In some embodiments, the weight ratio of zinc to CHP/CHP hydrate is 1:500 to about 50:1. In some embodiments, the weight ratio of zinc to CHP/CHP hydrate is 1:400 to about 50:1. In some embodiments, the weight ratio of zinc to CHP/CHP hydrate is 1:300 to about 50:1. In some embodiments, the weight ratio of zinc to CHP/CHP hydrate is 1:200 to about 50:1. In some embodiments, the weight ratio of zinc to CHP/CHP hydrate is 1:100 to about 50:1. In some embodiments, the weight ratio of zinc to CHP/CHP hydrate is 1:500 to about 30:1. In some embodiments, the weight ratio of zinc to CHP/CHP hydrate is 1:400 to about 30:1. In some embodiments, the weight ratio of zinc to CHP/CHP hydrate is 1:300 to about 30:1. In some embodiments, the weight ratio of zinc to CHP/CHP hydrate is 1:200 to about 30:1. In some embodiments, the weight ratio of zinc to CHP/CHP hydrate is 1:100 to about 30:1. In some embodiments, the weight ratio of zinc to CHP/CHP hydrate is 1:500 to about 10:1. In some embodiments, the weight ratio of zinc to CHP/CHP hydrate is 1:400 to about 10:1. In some embodiments, the weight ratio of zinc to CHP/CHP hydrate is 1:300 to about 10:1. In some embodiments, the weight ratio of zinc to CHP/CHP hydrate is 1:200 to about 10:1. In some embodiments, the weight ratio of zinc to CHP/CHP hydrate is 1:100 to about 10:1. In some embodiments, the weight ratio of zinc to CHP/CHP hydrate is 1:50 to about 5:1. In some embodiments, the weight ratio of zinc to CHP/CHP hydrate is 1:40 to about 5:1. In some embodiments, the weight ratio of zinc to CHP/CHP hydrate is 1:30 to about 5:1. In some embodiments, the weight ratio of zinc to CHP/CHP hydrate is 1:20 to about 5:1. In some embodiments, the weight ratio of zinc to CHP/CHP hydrate is 1:10 to about 5:1. Zinc as noted above relates to the amount of zinc cation.

In some embodiments, the weight ratio of zinc to CHP/CHP hydrate is from about 1:10 to about 100:1. In some embodiments, the weight ratio of zinc to CHP/CHP hydrate is from about 1:6 to about 5:1. In some embodiments, the weight ratio of zinc to CHP/CHP hydrate is from about 1:15 to about 20:1. In some embodiments, the weight ratio of zinc to CHP/CHP hydrate is from about 1:30 to about 4:1. In some embodiments, the weight ratio of zinc to CHP/CHP hydrate is from about 1:8 to about 4:1. In some embodiments, the weight ratio of zinc to CHP/CHP hydrate is from about 1:40 to about 40:1. Zinc as noted above relates to the amount of zinc cation. As referred to herein, numerical values for zinc represent masses or concentrations of the zinc component of a zinc salt or zinc compound. Examples of zinc salts useful in connection with the invention include zinc chloride, zinc acetate, zinc gluconate, zinc stearate, zinc sulfate, zinc oxide, zinc picolinate, zinc orotate, or zinc citrate.

In one embodiment, a composition may contain an amount of zinc cation ranging from about 1 to about 1000 mg, about 1 to about 800 mg, about 1 to about 700 mg, about 1 to about 600 mg, about 1 to about 500 mg, about 1 to about 400 mg, about 1 to about 300 mg, about 1 to about 200 mg, about 1 to about 100 mg, about 10 to about 300 mg, about 20 to about 200 mg, about 20 to about 100 mg, about 30 to about 100 mg. In one embodiment, CHP/CHP hydrate may be present in the same or a different composition in amount ranging from about 0.5 to about 1000 mg, about 0.5 to about 900 mg, about 0.5 to about 800 mg, about 0.5 to about 700 mg, about 0.5 to about 600 mg, about 0.5 to about 500 mg, about 0.5 to about 400 mg, about 0.5 to about 300 mg, about 0.5 to about 200 mg, about 0.5 to about 100 mg, about 0.5 to about 50 mg, from about 1 to 100 mg, from about 1 to 90 mg, from about 1 to 80 mg, from about 1 to 70 mg, from about 1 to 60 mg, from about 1 to 50 mg, from about 1 to 40 mg, from about 1 to 30 mg, from about 1 to 20 mg, from about 1 to 15 mg, from about 10 to 100 mg, from about 10 to 90 mg, from about 10 to 80 mg, from about 10 to 70 mg, from about 10 to 80 mg, from about 10 to 70 mg, from about 10 to 60 mg, or from about 10 to about 50 mg. In another embodiment, the amount of CHP/CHP hydrate present in the administered pharmaceutical composition can range from about 0.5 to about 100 mg, from about 5 to about 60 mg, or from about 10 to about 70 mg.

In certain embodiments, the zinc is administered to the mammal in an amount from about 0.01 to about 100 mg/kg/day. In one embodiment, a zinc is administered mammal in an amount from about 0.01 to about 50 mg/kg/day. In one embodiment, a zinc is administered mammal in an amount from about 0.01 to about 20 mg/kg/day. In one embodiment, a zinc is administered mammal in an amount from about 0.01 to about 15 mg/kg/day. In one embodiment, a zinc is administered mammal in an amount from about 0.01 to about 10 mg/kg/day. In another embodiment, a zinc is administered to the mammal in an amount from about 0.01 to about 0.4 mg/kg/day. In another embodiment, a zinc is administered to the mammal in an amount from about 0.1 to about 2 mg/kg/day. In another embodiment, a zinc is administered to the mammal in an amount from about 2 to about 4 mg/kg/day. In another embodiment, a zinc is administered to the mammal in an amount from about 1 to about 10 mg/kg/day. In another embodiment, a zinc is administered to the mammal in an amount from about 3 to about 8 mg/kg/day. In another embodiment, a zinc is administered to the mammal in an amount from about 4 to about 7 mg/kg/day. In another embodiment, a zinc cation of the zinc salt is administered to the mammal in an amount from about 7 to about 10 mg/kg/day. In another embodiment, a zinc is administered to the mammal in an amount from about 0.01 to about 0.18 mg/kg/day. In another embodiment, a zinc is administered to the mammal in an amount from about 0.5 to about 2 mg/kg/day. In another embodiment, a zinc is administered to the mammal in an amount from about 1 to about 1.5 mg/kg/day. Zinc as noted above relates to the amount of zinc cation.

In embodiments, CHP/CHP hydrate may be administered to the mammal in an amount from about 0.005 to about 1.5 mg/kg/day. In some embodiments, CHP/CHP hydrate is administered to the mammal in an amount from about 0.05 to about 15 mg/kg/day. In some embodiments, CHP/CHP hydrate is administered to the mammal in an amount from about 0.05 to about 10 mg/kg/day. In some embodiments, CHP/CHP hydrate is administered to the mammal in an amount from about 0.05 to about 5 mg/kg/day. In some embodiments, CHP/CHP hydrate is administered to the mammal in an amount from about 0.01 to about 2 mg/kg/day. In some embodiments, CHP/CHP hydrate is administered to the mammal in an amount from about 0.1 to about 5 mg/kg/day. In some embodiments, CHP/CHP hydrate is administered to the mammal in an amount from about 1 to about 15 mg/kg/day. In some embodiments, CHP/CHP hydrate is administered to the mammal in an amount from about 1 to about 10 mg/kg/day. In some embodiments, CHP/CHP hydrate is administered to the mammal in an amount from about 2 to about 7 mg/kg/day. In some embodiments, CHP/CHP hydrate is administered to the mammal in an amount from about 3 to about 5 mg/kg/day. In some embodiments, CHP/CHP hydrate is administered to the mammal in an amount from about 7 to about 10 mg/kg/day. In some embodiments, CHP/CHP hydrate is administered to the mammal in an amount from about 0.5 to about 2 mg/kg/day. In some embodiments, CHP/CHP hydrate is administered to the mammal in an amount from about 0.2 to about 4 mg/kg/day. In some embodiments, CHP/CHP hydrate is administered to the mammal in an amount from about 0.8 to about 3 mg/kg/day. In some embodiments, CHP/CHP hydrate is administered to the mammal in an amount from about 1 to about 6 mg/kg/day. The effective dose or CHP/CHP hydrate may be administered once or more per day for the period of five days to one or more months. The CHP/CHP hydrate may be administered simultaneously or sequentially with zinc or other antiviral agents.

In embodiments, CHP/CHP hydrate may be administered to the mammal in an amount from about 0.05 to about 15 mg/kg/day. In some embodiments, CHP/CHP hydrate is administered to the mammal in an amount from about 0.5 to about 150 mg/kg/day. In some embodiments, CHP/CHP hydrate is administered to the mammal in an amount from about 0.5 to about 100 mg/kg/day. In some embodiments, CHP/CHP hydrate is administered to the mammal in an amount from about 0.5 to about 50 mg/kg/day. In some embodiments, CHP/CHP hydrate is administered to the mammal in an amount from about 0.1 to about 20 mg/kg/day. In some embodiments, CHP/CHP hydrate is administered to the mammal in an amount from about 1 to about 50 mg/kg/day. In some embodiments, CHP/CHP hydrate is administered to the mammal in an amount from about 10 to about 150 mg/kg/day. In some embodiments, CHP/CHP hydrate is administered to the mammal in an amount from about 10 to about 100 mg/kg/day. In some embodiments, CHP/CHP hydrate is administered to the mammal in an amount from about 20 to about 70 mg/kg/day. In some embodiments, CRP/CRP hydrate is administered to the mammal in an amount from about 30 to about 50 mg/kg/day. In some embodiments, CHP/CHP hydrate is administered to the mammal in an amount from about 70 to about 100 mg/kg/day. In some embodiments, CHP/CHP hydrate is administered to the mammal in an amount from about 5 to about 20 mg/kg/day. In some embodiments, CHP/CHP hydrate is administered to the mammal in an amount from about 2 to about 40 mg/kg/day. In some embodiments, CHP/CHP hydrate is administered to the mammal in an amount from about 8 to about 30 mg/kg/day. In some embodiments, CHP/CHP hydrate is administered to the mammal in an amount from about 10 to about 60 mg/kg/day. The effective dose or CHP/CHP hydrate may be administered once or more per day for the period of five days to one or more months. The CHP/CHP hydrate may be administered simultaneously or sequentially with zinc or other antiviral agents.

In embodiments, CHP/CHP hydrate may be administered to the mammal in an amount from about 0.5 to about 150 mg/kg/day. In some embodiments, CHP/CHP hydrate is administered to the mammal in an amount from about 5 to about 1500 mg/kg/day. In some embodiments, CHP/CHP hydrate is administered to the mammal in an amount from about 5 to about 1000 mg/kg/day. In some embodiments, CHP/CHP hydrate is administered to the mammal in an amount from about 5 to about 500 mg/kg/day. In some embodiments, CHP/CHP hydrate is administered to the mammal in an amount from about 1 to about 200 mg/kg/day. In some embodiments, CHP/CHP hydrate is administered to the mammal in an amount from about 10 to about 500 mg/kg/day. In some embodiments, CHP/CHP hydrate is administered to the mammal in an amount from about 100 to about 1500 mg/kg/day. In some embodiments, CHP/CHP hydrate is administered to the mammal in an amount from about 100 to about 1000 mg/kg/day. In some embodiments, CHP/CHP hydrate is administered to the mammal in an amount from about 200 to about 700 mg/kg/day. In some embodiments, CHP/CHP hydrate is administered to the mammal in an amount from about 300 to about 500 mg/kg/day. In some embodiments, CHP/CHP hydrate is administered to the mammal in an amount from about 700 to about 1000 mg/kg/day. In some embodiments, CHP/CHP hydrate is administered to the mammal in an amount from about 50 to about 200 mg/kg/day. In some embodiments, CHP/CHP hydrate is administered to the mammal in an amount from about 20 to about 400 mg/kg/day. In some embodiments, CHP/CHP hydrate is administered to the mammal in an amount from about 80 to about 300 mg/kg/day. In some embodiments, CHP/CHP hydrate is administered to the mammal in an amount from about 100 to about 600 mg/kg/day. The effective dose or CHP/CHP hydrate may be administered once or more per day for the period of five days to one or more months. The CHP/CHP hydrate may be administered simultaneously or sequentially with zinc or other antiviral agents.

The mammals may be for example, cats, dogs, mice, guinea pigs, horses, cows, sheep, and humans.

In one embodiment for treatment of human beings, each tablet or capsule preferably contains about 1 to about 200 mg of zinc, preferably about 5 to about 50 mg zinc, and about 0.5 to about 200 mg of CHP, in addition to the pharmaceutically acceptable excipient or excipients. Thus, in an embodiment, a weight ratio of zinc cation to CHP is from about 1:100 to about 100:0.5. It is believed that compositions with these ratios of ingredients are effective in treating a wide range of mammals.

Treatment with CHP/CHP hydrate, alone or with zinc, can be conducted using two or more dosing phases: loading phase and maintenance phase. The loading phase can employ a relative higher dose (for example, including, but not being limited to, about 300 mg/kg/day to 500 mg/kg/day until steady state plasma levels of CHP/CHP hydrate and optionally zinc are achieved, and the maintenance phase can employ a dose of 100 mg/kg 150 mg/kg once daily or 50 mg/kg to 80 mg/kg twice daily.

In certain embodiments, the composition comprising zinc and CHP/CHP hydrate may be used to treat and/or prevent viral or virally-induced conditions. The virally-induced conditions may include such symptoms that include, but are not limited, fever, cough, shortness of breath, pain or pressure in the chest, muscle aches, sore throat, unexplained loss of taste or smell, diarrhea, headache. The viral condition or virally-induced condition is caused by an RNA virus including coronavirus such as MERS, SARS, SARS-CoV-2, human immunodeficiency virus, a herpes virus, a parvovirus, a coxsackie virus, a Human T-lymphotropic virus, a BK virus, or a hepatitis virus.

In non-limiting embodiments, the antiviral composition is administered to subjects having virally infected cells, wherein the cells exhibit an elevated ratio of alpha-3 to alpha-1 isoforms of Na,K-ATPase.

In non-limiting embodiments, the viral infection is caused by any of the following virus families: Arenaviridae, Arteriviridae, Bunyaviridae, Filoviridae, Flaviviridae, Orthomyxoviridae, Paramyxoviridae, Rhabdoviridae, Retroviridae (in particular, Deltaretrovirus genus), Coronaviridae, or Togaviridae. In some embodiments, the viral infection is caused by (+)-ss-envRNAV or (−)-ss-envRNAV.

Non-limiting embodiments are directed to compositions for and methods of treating Filovirus infection, Flavivirus infection, Henipavirus infection, alphavirus infection, or Togavirus infection. Viral infections that can be treated include, at least, Ebolavirus, Marburgvirus, Alphavirus, Flavivirus, Yellow Fever, Dengue Fever, Japanese Enchephalitis, West Nile Viruses, Zikavirus, Venezuelan Equine Encephalomyelitis (encephalitis) (VEE) virus, Chikungunya virus, Western Equine Encephalomyelitis (encephalitis) (WEE) virus, Eastern Equine Encephalomyelitis (encephalitis) (EEE) virus, Tick-borne Encephalitis, Kyasanur Forest Disease, Alkhurma Disease, Omsk Hemorrhagic Fever, Hendra virus, Nipah virus, Deltaretrovirus genus, HTLV-1 virus, and species thereof.

Non-limiting embodiments are directed to compositions for and methods of treating viral infections from viruses of the Arenaviridae family, Arteriviridae, Bunyaviridae family, Filoviridae family, Flaviviridae family (Flavivirus genus), Orthomyxoviridae family, Paramyxoviridae family, Rhabdoviridae family, Retroviridae family (Deltaretrovirus genus), Coronaviridae family, (+)-ss-envRNAV, (−)-ss-envRNAV, or Togaviridae family.

Non-limiting embodiments are directed to compositions for and methods of treating viral infections from viruses of the Henipavirus genus, Ebolavirus genus, Flavivirus genus, Marburgvirus genus, Deltaretrovirus genus, Coronavirus (CoV), or Alphavirus genus.

In some embodiments, the (+)-ss-envRNAV is a virus selected from the group consisting of Coronaviridae family, Flaviviridae family, Togaviridae family, and Arterviridae family.

In some embodiments, the (+)-ss-envRNAV may be a coronavirus that is pathogenic to humans. In some embodiments, the coronavirus spike protein binds to ACE2 (angiotensin converting enzyme 2) receptors in human tissue. In some embodiments, the coronavirus is selected from the group consisting of SARS-CoV, MERS-CoV, SARS-CoV-2 (COVID-19), CoV 229E, CoV NL63, CoV 0C43, CoV HKU1, and CoV HKU20.

In some embodiments, the (+)-ss-envRNAV may be a virus selected from the group consisting of flavivirus, Yellow Fever virus, Dengue Fever virus, Japanese Encephalitis virus, West Nile virus, Zikavirus, Tick-borne Encephalitis virus, Kyasanur Forest Disease virus, Alkhurma Disease virus, Omsk Hemorrhagic Fever virus, and Powassan virus.

In some embodiments, the (+)-ss-envRNAV may be a Togaviridae family virus selected from the group consisting of arborvirus, eastern equine encephalomyelitis virus (EEEV), western equine encephalomyelitis virus (WEEV), Venezuelan equine encephalomyelitis virus (VEEV), Chikungunya virus (CHIKV), O'nyong'nvirus (ONNV), Pogosta disease virus, Sindbis virus, Ross River fever virus (RRV) and Semliki Forest virus.

In some embodiments, the (−)-(ss)-envRNAV may be a virus selected from the group consisting of Arenaviridae family, Bunyaviridae family (Bunyavirales order), Filoviridae family, Orthomyxoviridae family, Paramyxoviridae family, or Rhabdoviridae family.

Some embodiment provides a method of treating coronavirus infection, in particular SARS-CoV-2 infection, by repeatedly administering to a subject having said infection an effective amount of CHP/CHP hydrate and optionally with zinc. One or more doses may be administered per day for one or more days per week and optionally for one or more weeks per month and optionally for one or more months per year.

The exemplary embodiment is directed to a method of treating coronavirus infection in a human, the method comprising administering to the subject 1-10 doses of CHP/CHP hydrate and optionally zinc per day for a treatment period of 2 days to about 2 months. Two to eight, two to six, or four doses can be administered daily during the treatment period until the viral infection is treated. Doses can be administered for 2 days to about 60 days, 2 days to about 45 days, 2 days to about 30 days, 2 days to about 21 days, or 2 days to about 14 days. The administering can be through any of the modes of administration discussed herein. In some embodiments, a composition for treating viral infection is provided. The composition comprises CHP/CHP hydrate as an effective ingredient and optionally zinc. In certain embodiments, the composition may be a pharmaceutical composition and comprises known pharmaceutically acceptable excipients. In certain embodiments, the composition may be a foodstuff or beverage and comprises known food additives or beverage additives. In certain embodiments, the composition may be a dietary supplement and comprise a pharmaceutically acceptable excipients. In embodiment, the viral infection could SARS-CoV-2 (COVID-19) infection. The composition can be administered systemically. Modes of systemic administration include parenteral, buccal, enteral, intramuscular, subdermal, sublingual, peroral, pulmonary, or oral. The composition can also be administered via injection or intravenously. The composition may also be administered by two or more routes to the same subject. In some embodiments, the composition is administered by a combination of any two or more modes of administration selected from the group consisting of parenteral, buccal, enteral, intramuscular, subdermal, sublingual, peroral, pulmonary, and oral. In some embodiments, a sublingual dosage form of the composition may be in a tablet, a liquid, or a film or strip form.

The method and composition according to an embodiment may comprise further administering an additional anti-viral agent. The additional anti-viral agent may be exemplified by, but not limited thereto, acyclovir, adapromine, amantadine, baloxavir marboxil, DRACO, favipiravir, FGI-106, galidesivir, GS-6620, ganciclovir, IDX-184, lumicitabine, meriticitabine, MK-608, moroxydine, mozenavir, NITD008, pimodivir, pleconaril, presatovir, remdesivir, ribavirin, rintatolimod, taribavirin, umifenovir, uprifosbuvir, valganciclovir, valopicitabine, nafamostat, nafamostat mesylate, a combination of nafamostat and heparin, oseltamivir, peramivir, rimantadine, zanamivir, or ziresovir.

In some embodiments, a weight ratio (w/w) between a CHP+zinc and an antiviral agent may range from about 1:0.01 to about 1:10, about 1:0.02 to about 1:10, about 1:0.02 to about 1:10, about 1:0.03 to about 1:10, about 1:0.04 to about 1:10, about 1:0.05 to about 1:10, about 1:0.06 to about 1:10, about 1:0.07 to about 1:10, about 1:0.08 to about 1:10, about 1:0.09 to about 1:10, about 1:0.1 to about 1:10, about 1:0.01 to about 1:5, about 1:0.02 to about 1:5, about 1:0.02 to about 1:5, about 1:0.03 to about 1:5, about 1:0.04 to about 1:5, about 1:0.05 to about 1:5, about 1:0.06 to about 1:5, about 1:0.07 to about 1:5, about 1:0.08 to about 1:5, about 1:0.09 to about 1:5, about 1:0.1 to about 1:5, about 1:0.1 to about 1:5, about 1:0.01 to about 1:1, about 1:0.02 to about 1:1, about 1:0.02 to about 1:1, about 1:0.03 to about 1:1, about 1:0.04 to about 1:1, about 1:0.05 to about 1:1, about 1:0.06 to about 1:1, about 1:0.07 to about 1:1, about 1:0.08 to about 1:1, about 1:0.09 to about 1:1, about 1:0.1 to about 1:1, about 1:0.01 to about 1:0.5, about 1:0.02 to about 1:0.5, about 1:0.02 to about 1:0.5, about 1:0.03 to about 1:0.5, about 1:0.04 to about 1:0.5, about 1:0.05 to about 1:0.5, about 1:0.06 to about 1:0.5, about 1:0.07 to about 1:0.5, about 1:0.08 to about 1:0.5, about 1:0.09 to about 1:0.5, about 1:0.1 to about 1:0.5, about 1:0.01 to about 1:0.7, about 1:0.02 to about 1:0.7, about 1:0.07 to about 1:0.7, about 1:0.03 to about 1:0.7, about 1:0.04 to about 1:0.7, about 1:0.05 to about 1:0.7, about 1:0.06 to about 1:0.7, about 1:0.07 to about 1:0.7, about 1:0.08 to about 1:0.7, about 1:0.09 to about 1:0.7, about 1:0.1 to about 1:0.7, about 1:0.01 to about 1:0.6, about 1:0.02 to about 1:0.6, about 1:0.02 to about 1:0.6, about 1:0.03 to about 1:0.6, about 1:0.04 to about 1:0.6, about 1:0.05 to about 1:0.6, about 1:0.06 to about 1:0.6, about 1:0.07 to about 1:0.6, about 1:0.08 to about 1:0.6, about 1:0.09 to about 1:0.6, about 1:0.1 to about 1:0.6, about 1:0.01 to about 1:0.8, about 1:0.02 to about 1:0.8, about 1:0.02 to about 1:0.8, about 1:0.03 to about 1:0.8, about 1:0.04 to about 1:0.8, about 1:0.05 to about 1:0.8, about 1:0.06 to about 1:0.8, about 1:0.07 to about 1:0.8, about 1:0.08 to about 1:0.8, about 1:0.09 to about 1:0.8, about 1:0.1 to about 1:0.8, about 1:0.01 to about 1:0.9, about 1:0.02 to about 1:0.9, about 1:0.02 to about 1:0.9, about 1:0.03 to about 1:0.9, about 1:0.04 to about 1:0.9, about 1:0.05 to about 1:0.9, about 1:0.06 to about 1:0.9, about 1:0.07 to about 1:0.9, about 1:0.08 to about 1:0.9, or about 1:0.09 to about 1:0.9, about 1:0.1 to about 1:0.9. In some embodiments, the antiviral agent may be remdesivir. In some embodiments, for example, about 15 mg of CHP+zinc may be administered in combination with about 0.5-15 mg, about 1-15 mg, or about 1.5-15 mg of remdesivir. In some embodiments, the 15 mg of CHP+zinc may include about 5 mg of CHP and about 10 mg of zinc.

A steroid was reported to improve survival rates for severe cases of SARS-CoV-2 infected patients, for example those on ventilators or suffering from pulmonary infections. It is speculated that patients with severe cases of SARS-CoV-2 infection have dangerously high levels of inflammation as part of an overactive immune response to the virus and that calming that down with an anti-inflammatory drug could help ease the symptoms. An example of steroid may include dexamethasone, methylprednisolone, or hydrocortisone. In one embodiment, steroid is dexamethasone. In an embodiment, a low-dose steroid (e.g. about 0.1-10 mg/kg/day (e.g., about 1 mg/kg/day) methylprednisolone or about 1-50 mg/day, or about 1-10 mg/day dexamethasone) can be employed. In an embodiment, steroid benefit may be greatest ~5-10 days after onset of symptoms, during the beginning of the adaptive immunity phase.

Certain aspects of the invention can be described in greater detail in the non-limiting Examples that follows. The following examples are included to demonstrate certain embodiments of the present disclosure. Those of skill in the art should, however, in light of the present disclosure, appreciate that modifications can be made in the specific embodiments that are disclosed and still obtain a like or similar result without departing from the spirit and scope of the intention. Therefore, all matter set forth is to be interpreted as illustrative and not in a limiting sense.

EXAMPLES

Reference Example 1

Conversion of Pattern 1 (Anhydrous CHP) to Pattern 2 (CHP Hydrate)

An amount of 2 g of Pattern 1 material (Lot No PS00726-55-D) was dissolved in 1 mL water at 80° C. In order to counter a significant amount of evaporation, another 1 mL of water was added. At 80° C., this resulted in a clear, dark brown solution. Next, the solution was rapidly cooled to 50° C. and 9.5 volumes (19 mL) of acetone was added to the solution, to yield a pale yellow solution. No oiling or precipitation was detected. The solution was cooled to room temperature, resulting in a noticeable quantity of solid precipitation. The solution was cooled to 6° C. (to boost yield) and the slurry was filtered. The solid was dried on the filter to prevent dehydration. Because the dehydration to Patten 1 happens at 80° C. or higher under vacuum, drying at 50° C. under vacuum was considered to be safe to preserve Pattern 2. XRPD confirmed that the product is Pattern 2, with a yield of approximately 72%.

A batch of CHP Hydrate was analyzed by various techniques including: X-ray powder diffraction (XRPD), pKa analysis, polarized light microscopy (PLM), thermogravimetric analysis/differential thermal analysis (TG/DTA), differential scanning calorimetry (DSC), Fourier-transform infrared spectroscopy (FT-IR), dynamic vapor sorption (DVS), variable temperature and humidity X-ray powder diffractometry (VT-/VH-XRPD), $^1$H nuclear magnetic resonance (NMR), and heteronuclear single quantum coherence (HSQC) NMR.

A. X-ray Powder Diffraction (XRPD)

XRPD analysis was carried out on a PANalytical X'pert pro, scanning the samples between 3 and 35° 2θ. The material was gently ground to release any agglomerates and loaded onto a multi-well plate with Kapton or Mylar polymer film to support the sample. The multi-well plate was then placed into the diffractometer and analysed using Cu K radiation (α1λ=1.54060 Å; α2=1.54443 Å; β=1.39225 Å; α1:α2 ratio=0.5) running in transmission mode (step size 0.0130° 2θ) using 40 kV/40 mA generator settings.

Figure 2:
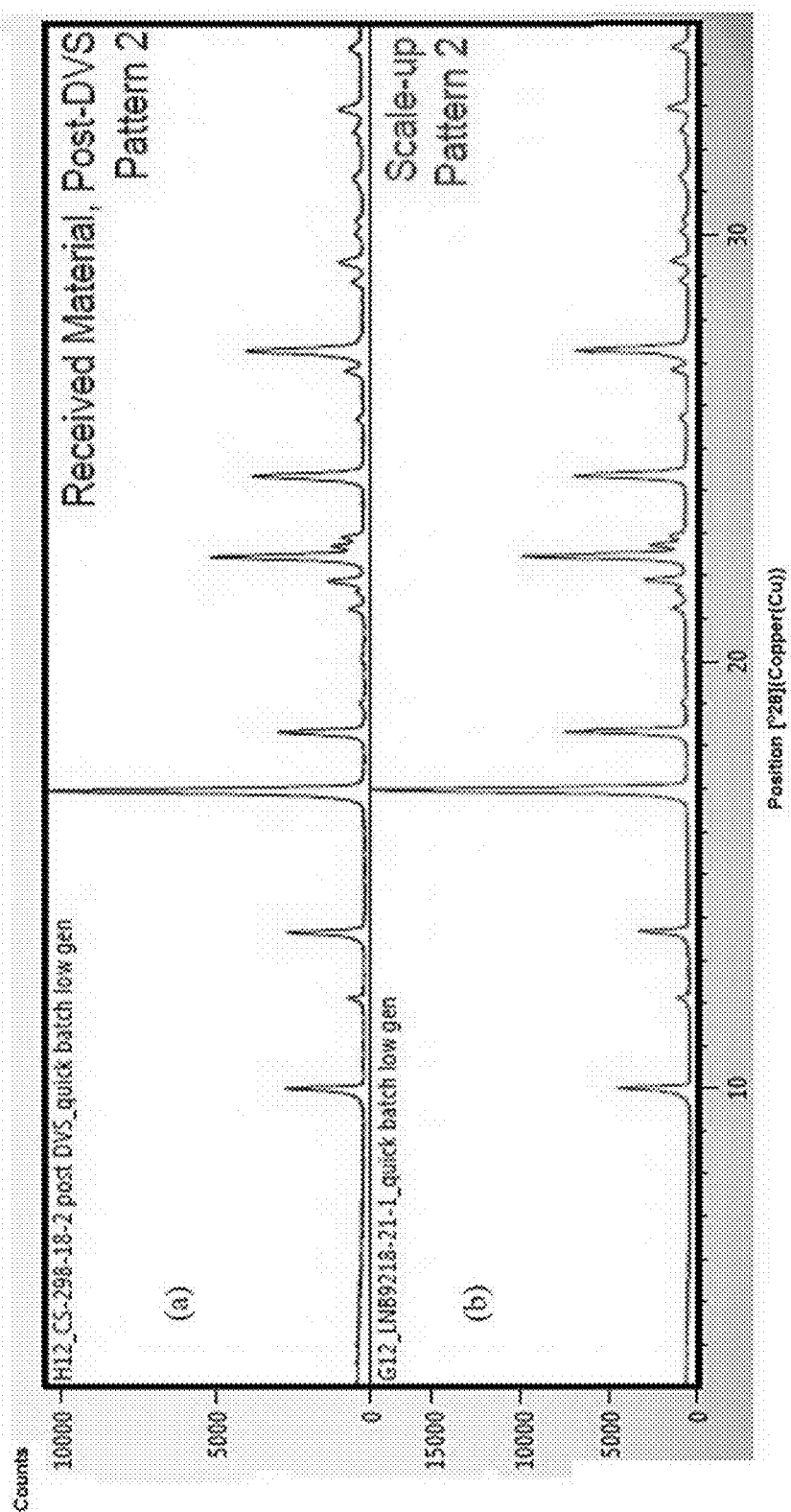
FIG. 2 is a comparison of the XRPD of (a) Pattern 1 post dynamic vapor sorption (DVS) and (b) the CHP hydrate ("Pattern 2"). These results confirm that the prepared CHP material is CHP hydrate and that Pattern 1 changed to Pattern 2 post-DVS.
Figure 3:
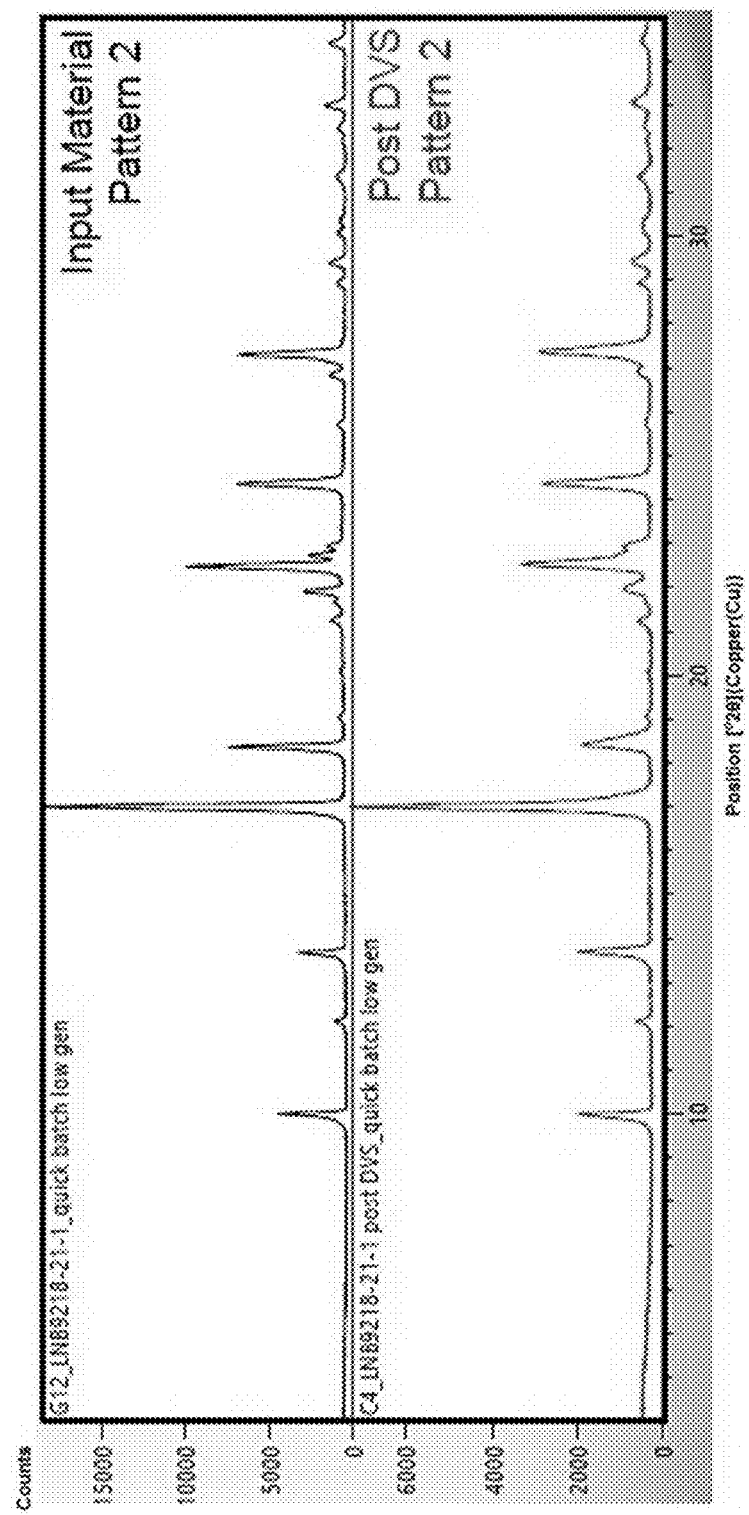
FIG. 3 is a comparison of the X-ray powder diffractograms of CHP hydrate (Pattern 2) at 40% RH pre-DVS and post-DVS.
Figure 4:
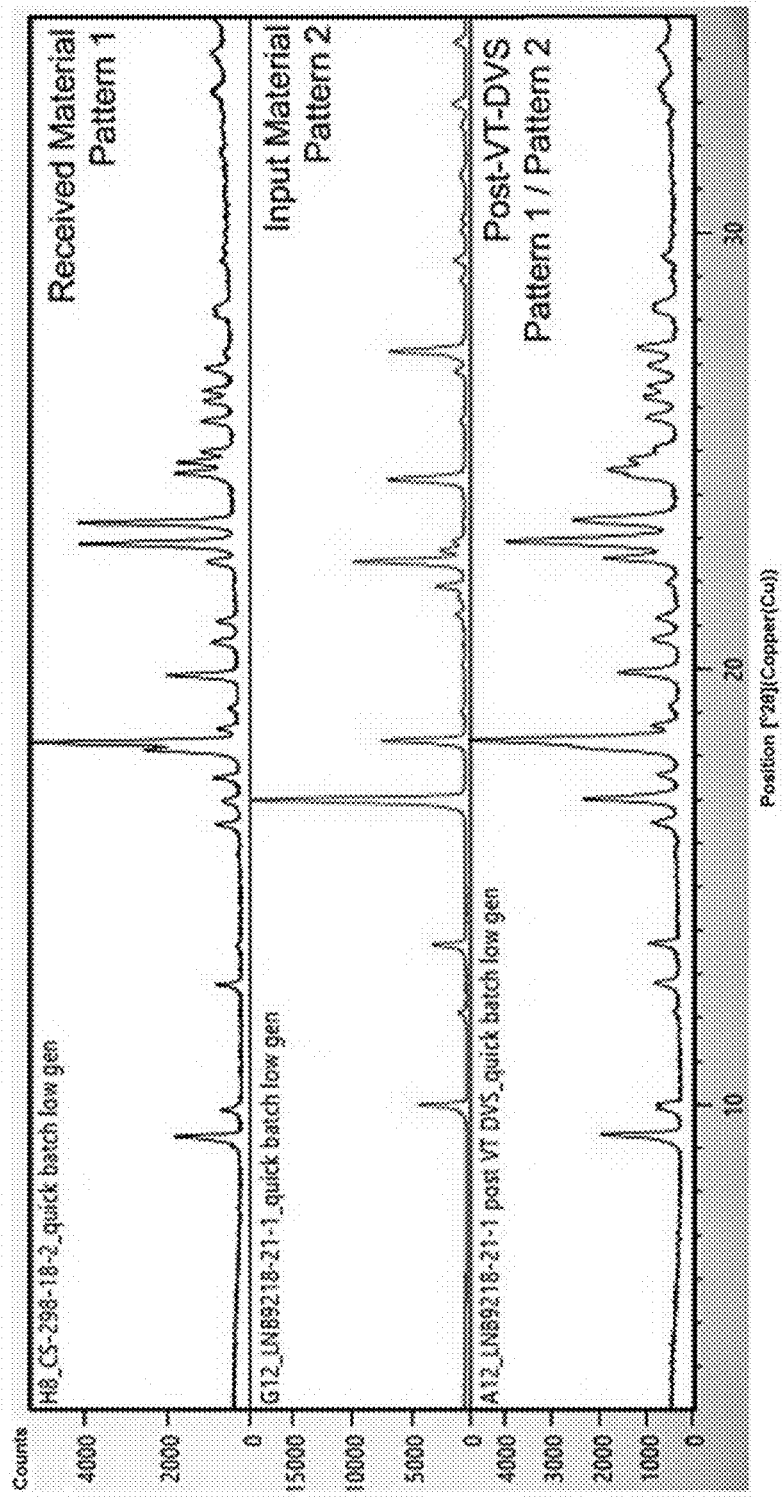
FIG. 4 is the analysis of the X-ray powder diffractograms of CHP hydrate (Pattern 2) post-VT-DVS. It shows that the material was a mixture of Patterns 1 and 2.
Figure 5:
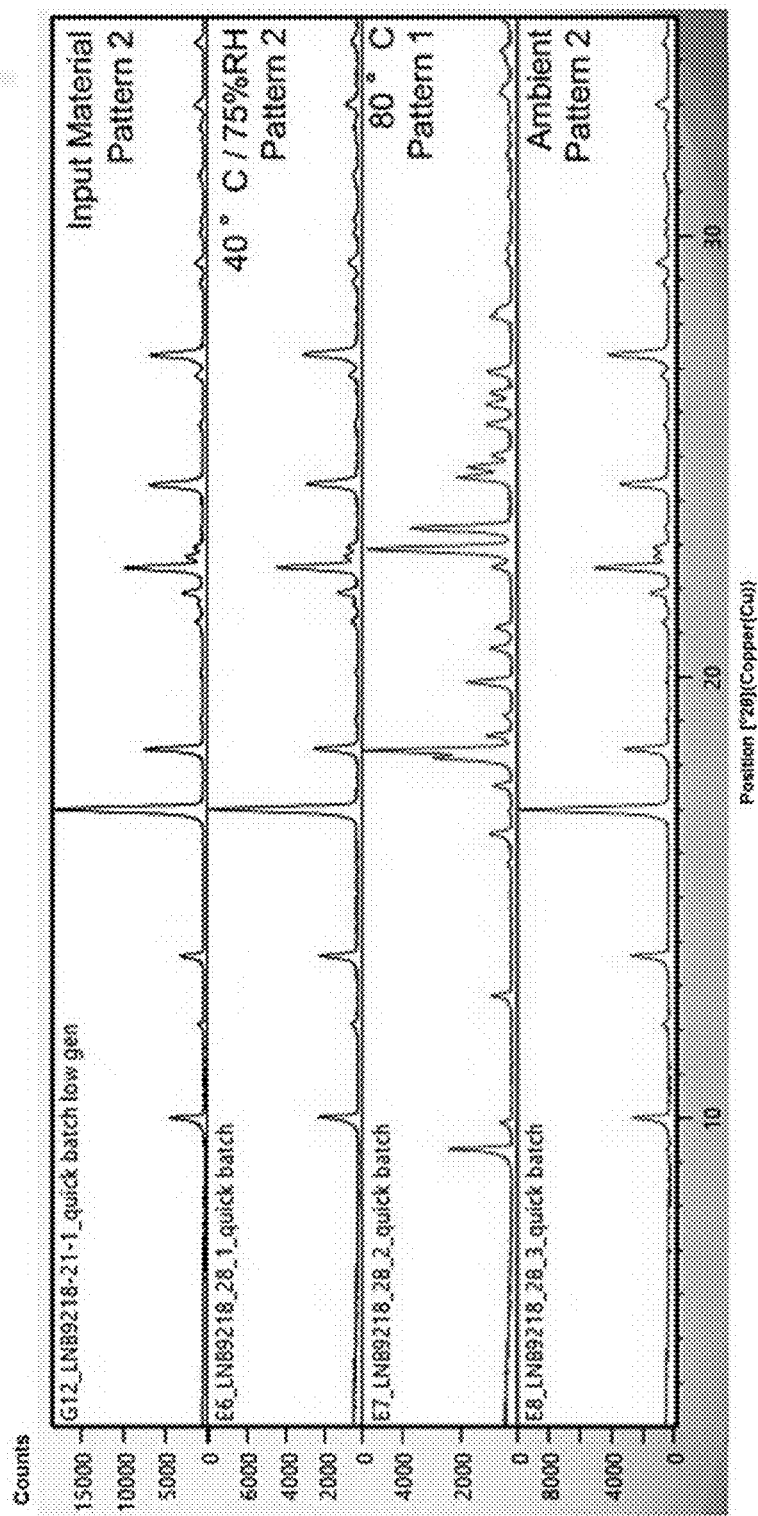
FIG. 5 is a comparison of the X-ray powder diffractograms of about 30 mg of CHP hydrate (Pattern 2) that was stored under three conditions for seven days: 40° C./75% RH, 80° C., and ambient light.
Figure 6:
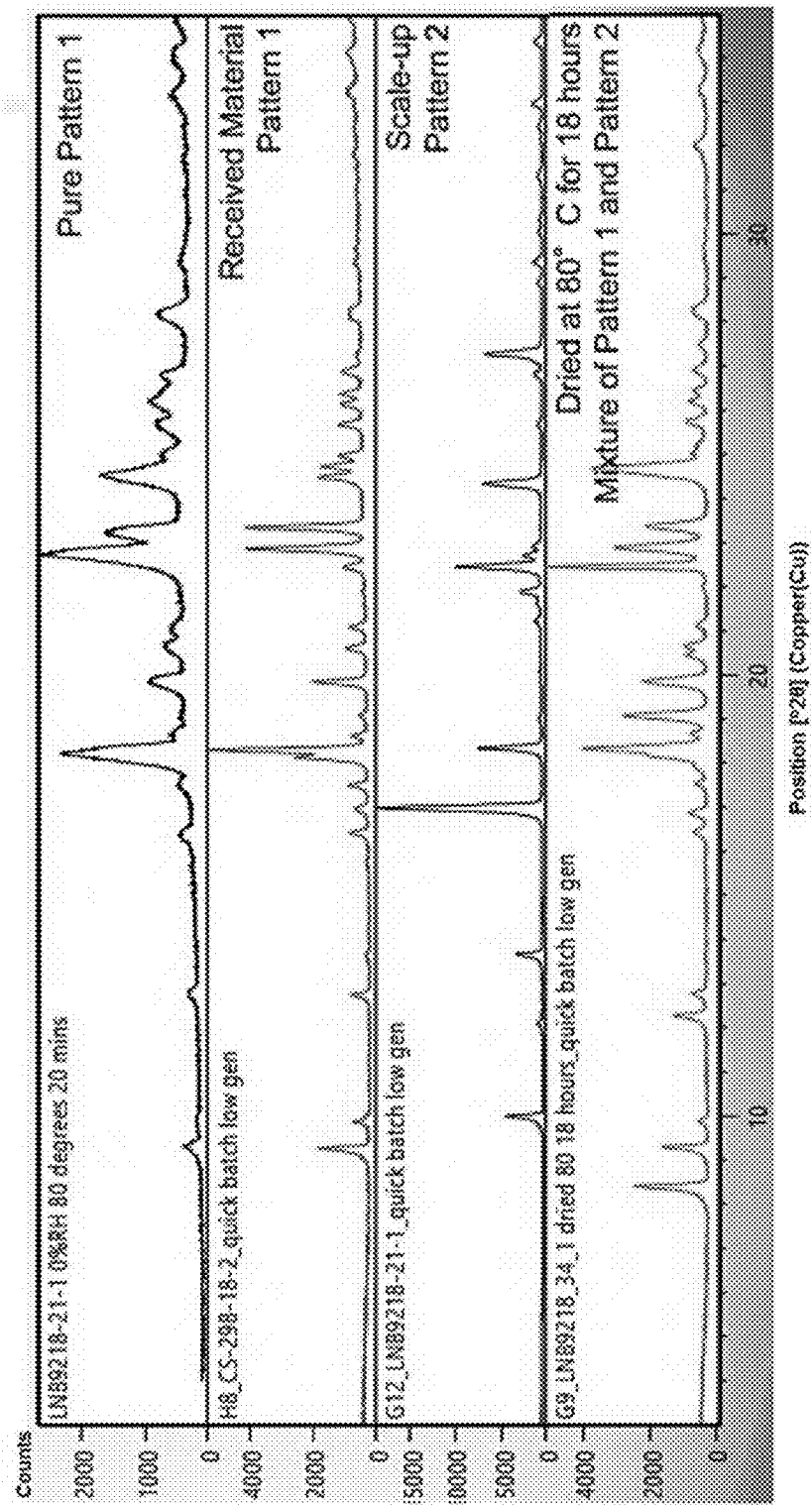
Figure 7:
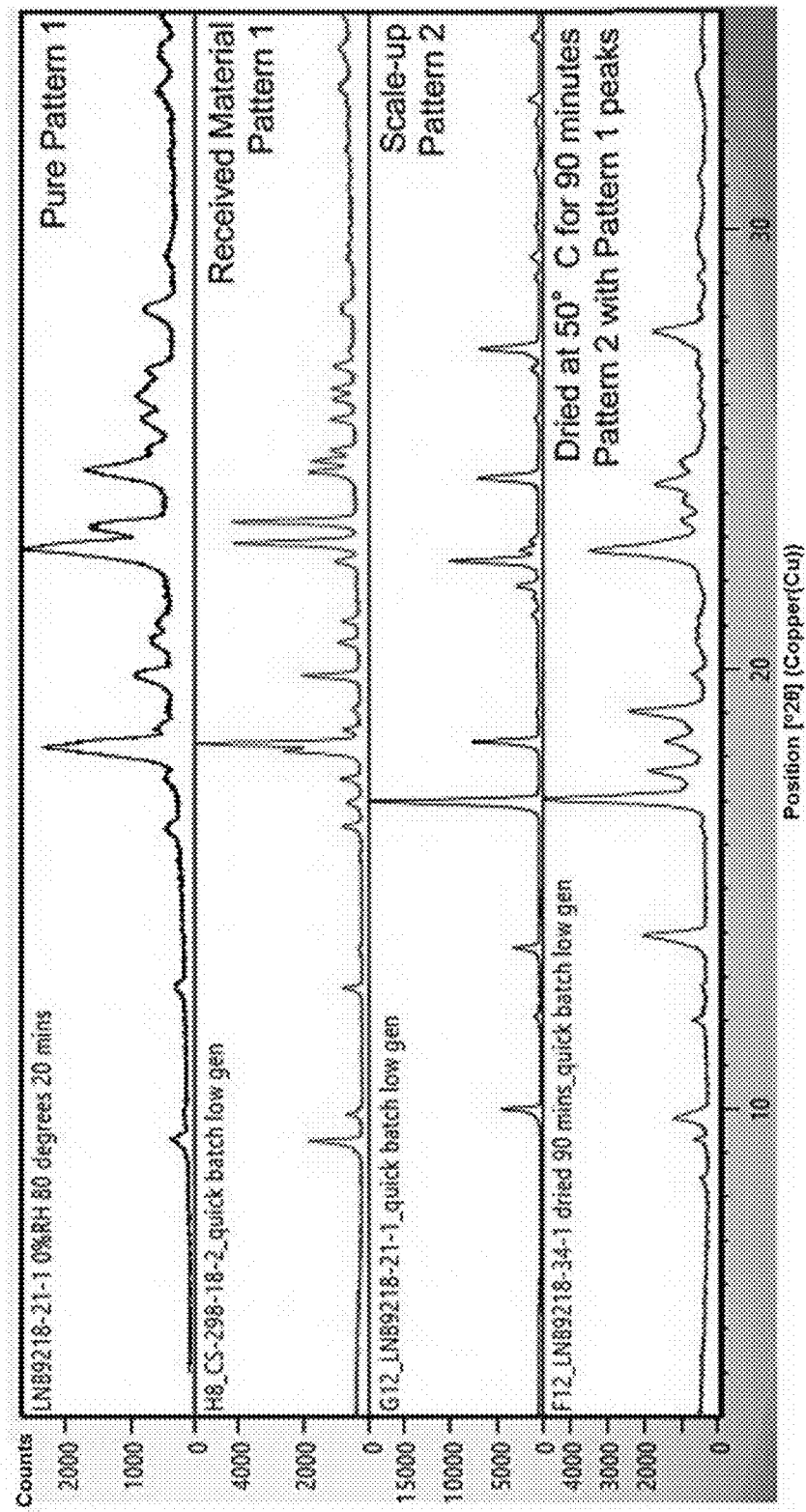

As shown in FIG. 1, the batch was crystalline by XRPD and was assigned as Pattern 1. XRPD analysis was carried out on a sample of 5 g of CHP Hydrate. The sample was weighed in a glass vial, and 6 mL of a 90:10 ethanol/water mixture was added to make a slurry. The mixture was then agitated for approximately 24 hours at ambient temperature and then analyzed by XRPD. As shown in FIG. 2, this material was confirmed as Pattern 2 (graph (b)). As shown in FIG. 3, the analysis of Pattern 2 following DVS showed no change in form at 40% RH post-DVS. As shown in FIG. 4, the analysis of Pattern 2 showed that post various temperature DVS (VT-DVS), the material was a mixture of Patterns 1 and 2. As shown in FIG. 5, approximately 30 mg of Pattern 2 (the top graph, FIG. 5) was stored under three conditions for seven days: 40° C./75% RH, 80° C., and ambient light. XPRD analysis was carried out to assess any change in the form of the material. After seven days, no change was observed in the samples stored at 40° C./75% RH (second graph from the top FIG. 5) and those stored at ambient light (bottom graph, FIG. 5). The sample stored at 80° C. converted to Pattern 1 (third graph from the top, FIG. 5). As shown in FIG. 6, when the Pattern 2 sample (third graph from the top of FIG. 6) was dried at 80° C. for 18 hours, XRPD analysis (bottom graph of FIG. 6) showed a mixture of Pattern 1 and Pattern 2. Referring to FIG. 7, when the Pattern 2 same was dried at 50° C. for 90 minutes (bottom graph of FIG. 7) showed the material was still predominantly Pattern 2 with some Pattern 1 peaks.

Figure 8:
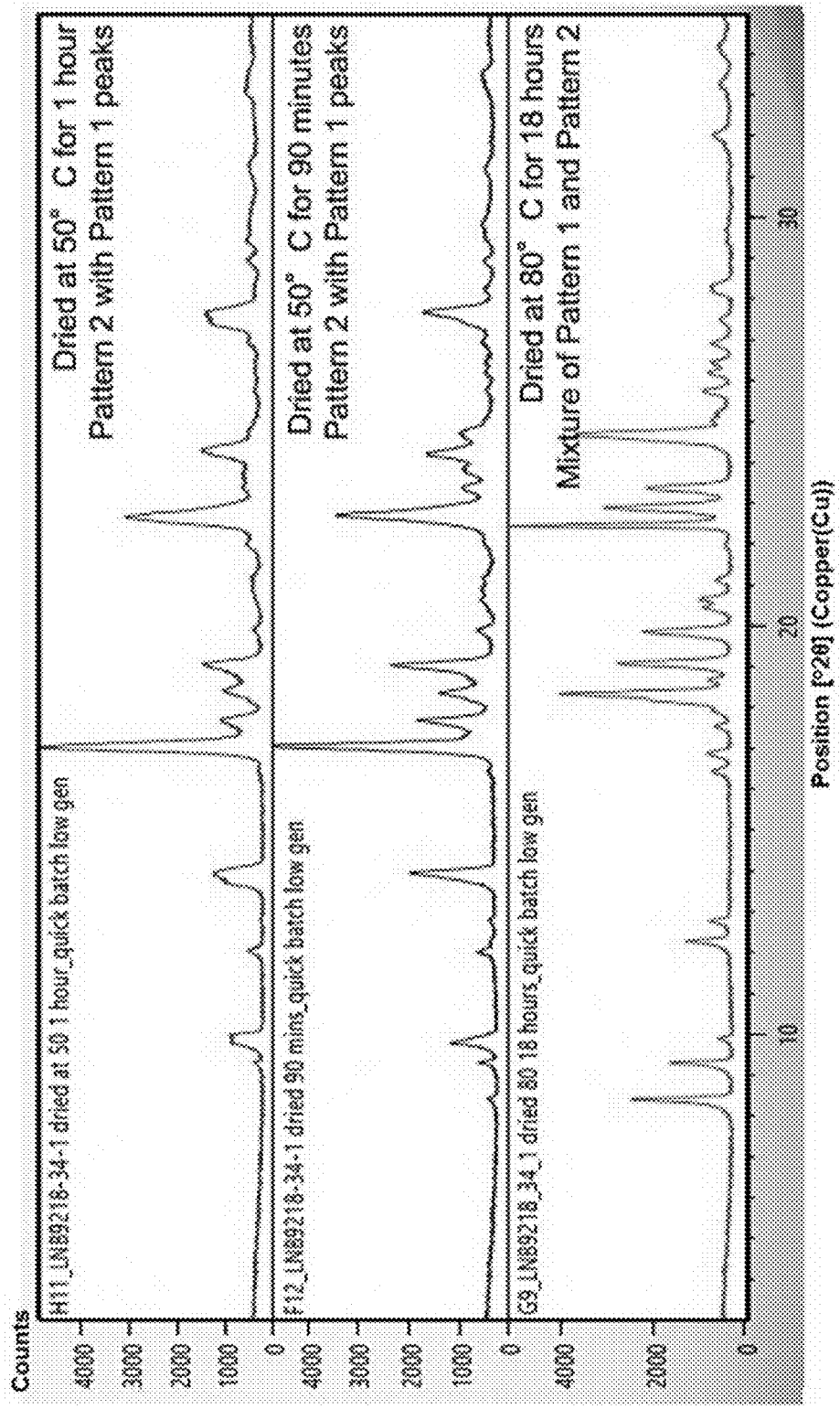
FIG. 8 is comparison of changes in Pattern 2 at different temperatures. It is an overlay of the product XRPD analysis of the sample from FIGS. 5-7 that was dried for three different time periods, and the results were analyzed by XRPD. The top graph represents Pattern 2 sample stored at 50° C. for 1 hour, the middle graphs represents Pattern 2 sample stored at 50° C. for 90 min, and the bottom graphs represents the Pattern 2 sample stored at 80° C. for 18 hours.
Figure 9:
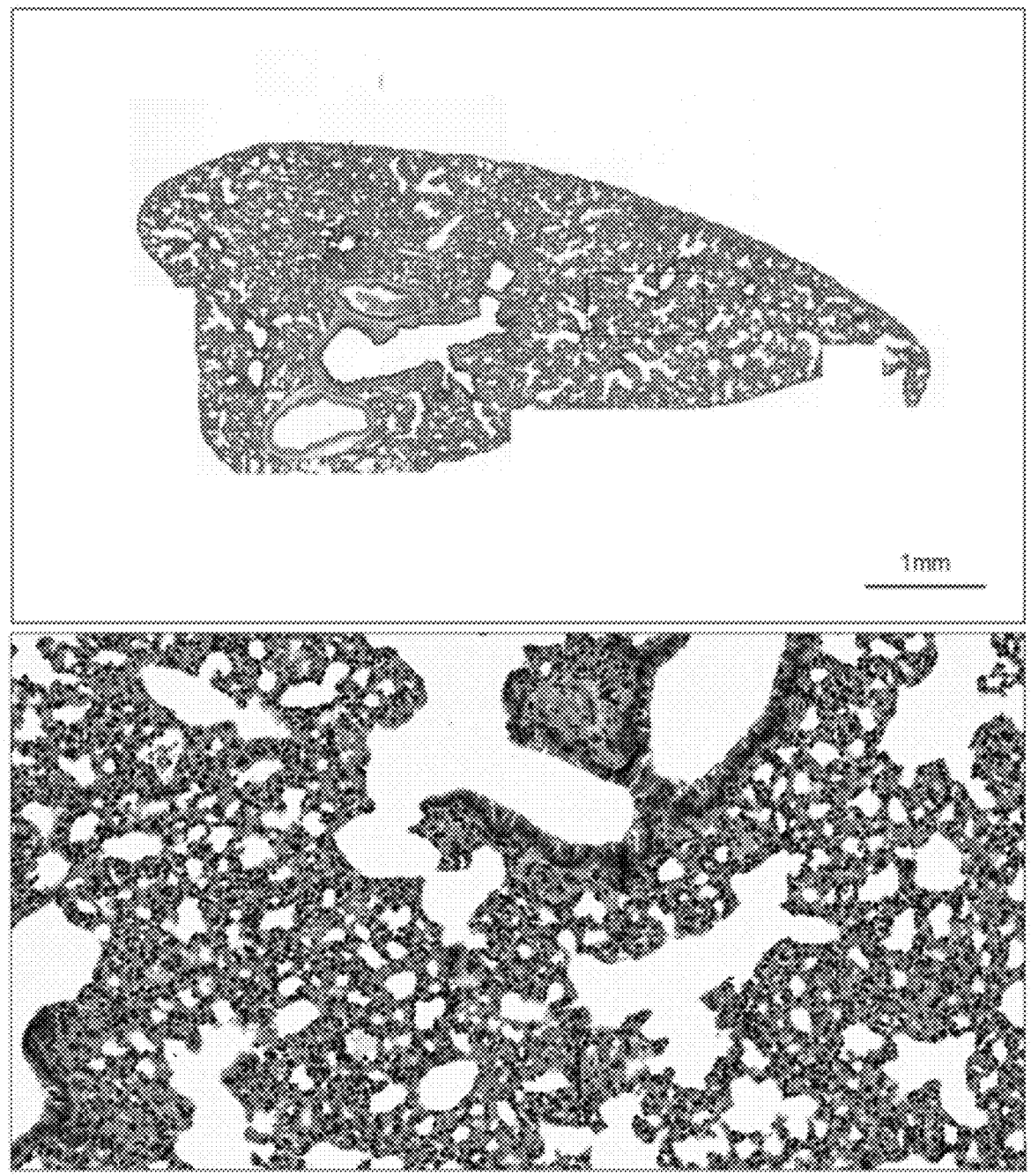
FIG. 9 is a microscopic image of lung tissue of a normal healthy subject who is not infected with SARS-CoV-2 virus.
Figure 10:
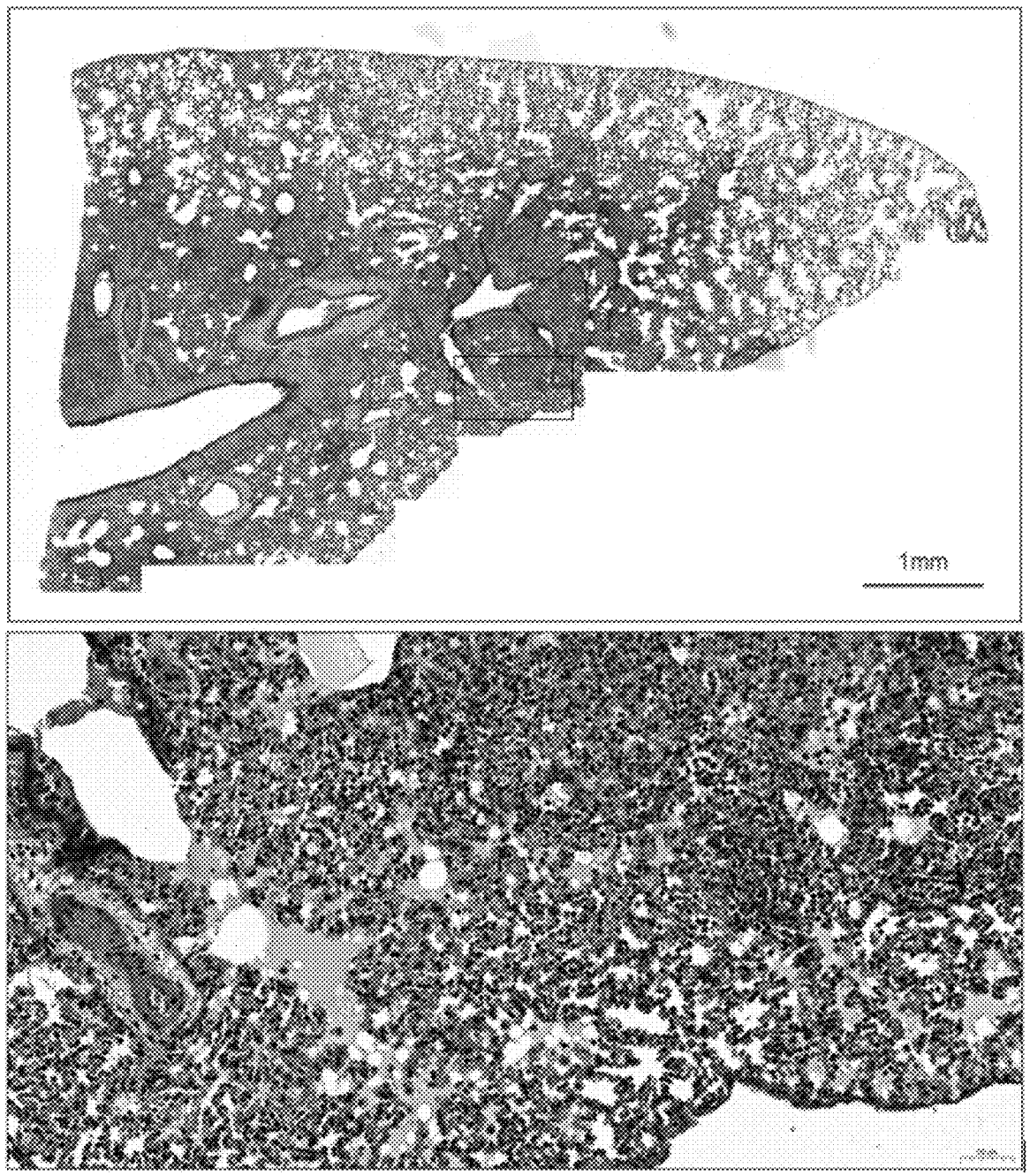
FIG. 10 is a microscopic image of lung tissue of a subject infected with SARS-CoV-2 virus and administered with a vehicle (control).
Figure 11:
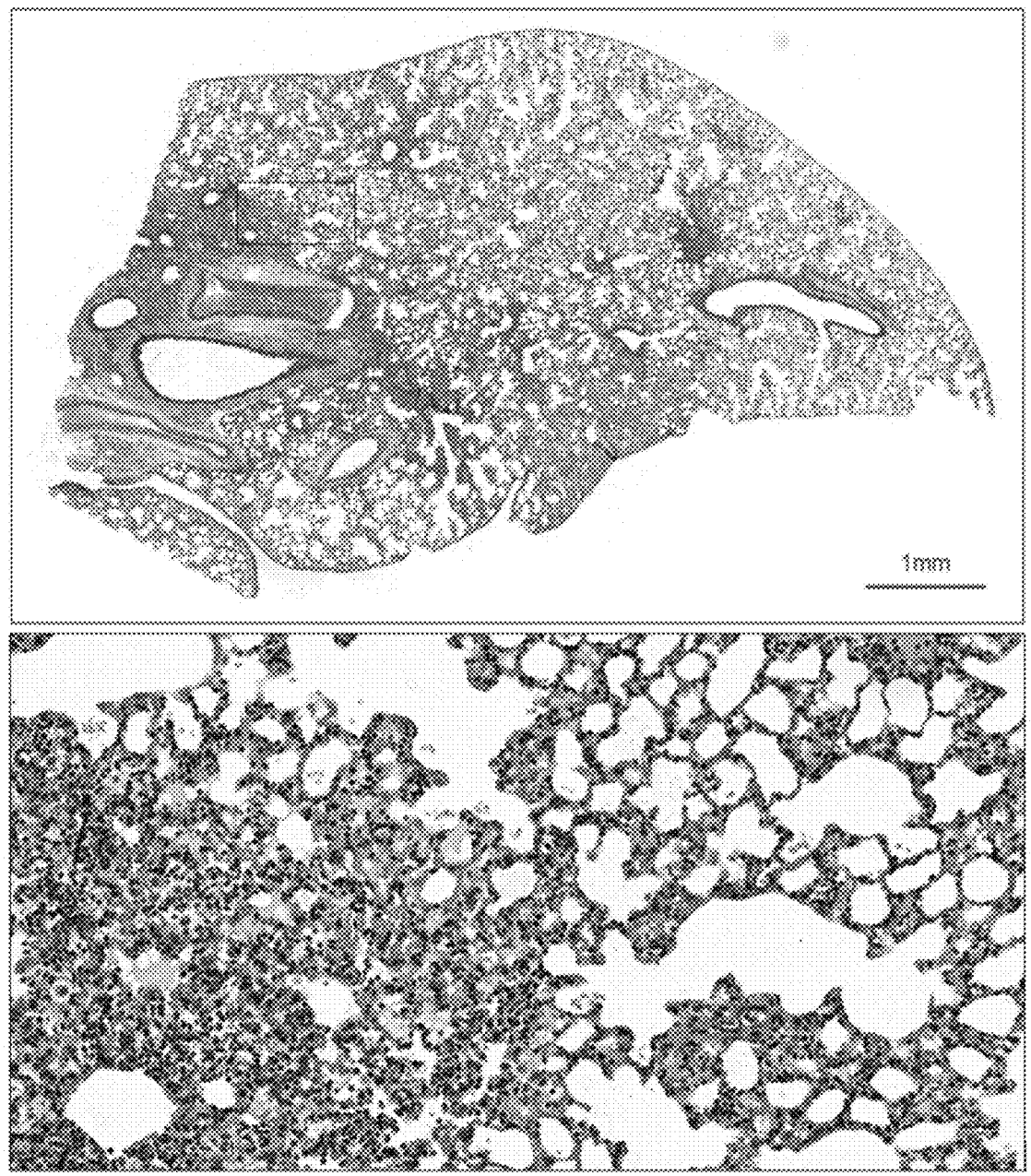
FIG. 11 is a microscopic image of lung tissue of a subject infected with SARS-CoV-2 virus and administered with a composition comprising a CRP and zinc.
Figure 12:
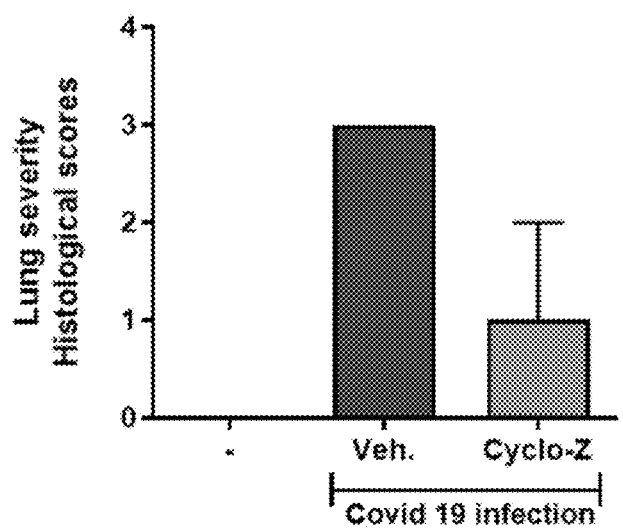
FIG. 12 shows lung damage severity (histological scores) of the subject who is infected with SRS-CoV-2 and treated with either vehicle (veh group) or a composition comprising a CHP and zinc (Cyclo-Z group).
Figure 13:
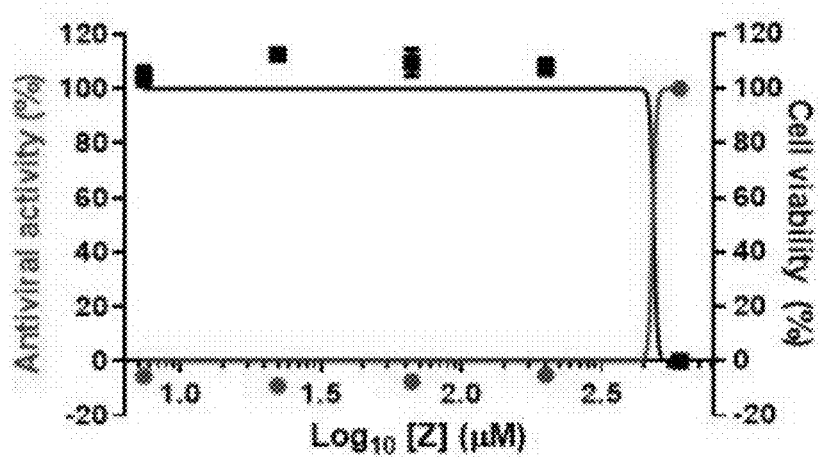
FIGS. 13-17 show the results of antiviral activity (-●-) and cytotoxicity (-■-) of zinc (600 μM, 200 μM, 67 μM, 22 μM, 7.4 μM) (FIG. 13); CHP (30 mM, 10 mM, 3.3 mM, 1.1 mM, 0.37 mM) (FIG. 14); zinc+CHP (600 μM+30 mM, 200 μM+10 mM, 67 μM+3.3 mM, 22 μM+1.1 mM, 7.4 μM+0.37 mM) (FIG. 15); zinc+CHP/chloroquine (600 μM+30 mM/20 μM, 200 μM+10 mM/20 μM, 67 μM+3.3 mM/20 μM, 22 M+1.1 mM/20 μM, 7.4 μM+0.37 mM/20 μM) (FIG. 16); chloroquine (100 μM, 33 μM, 11 M, 3.7 μM, 1.2 μM) (FIG. 17), respectively, as explained in Biological Examples.
Figure 14:
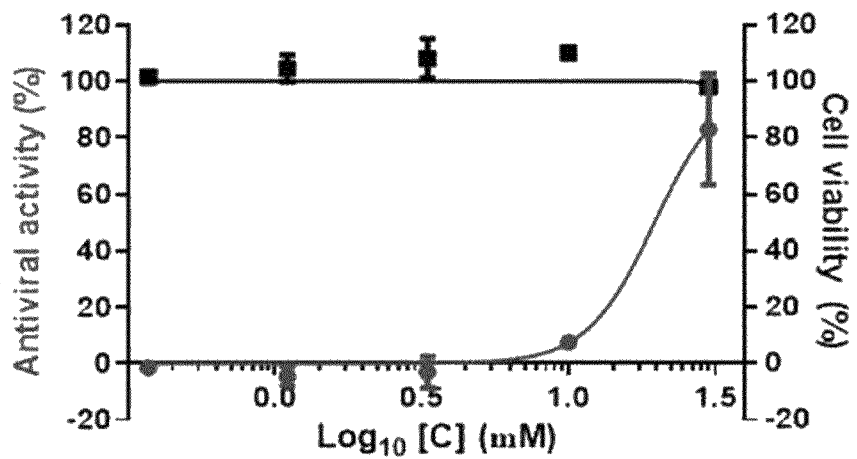
Figure 15:
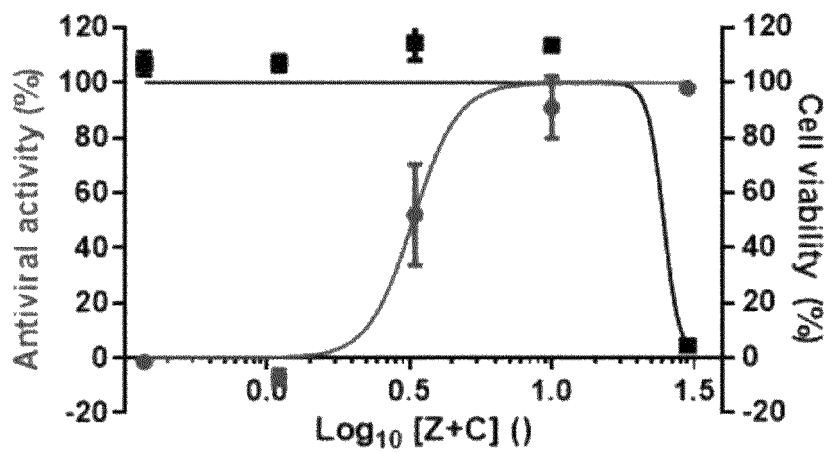
Figure 16:
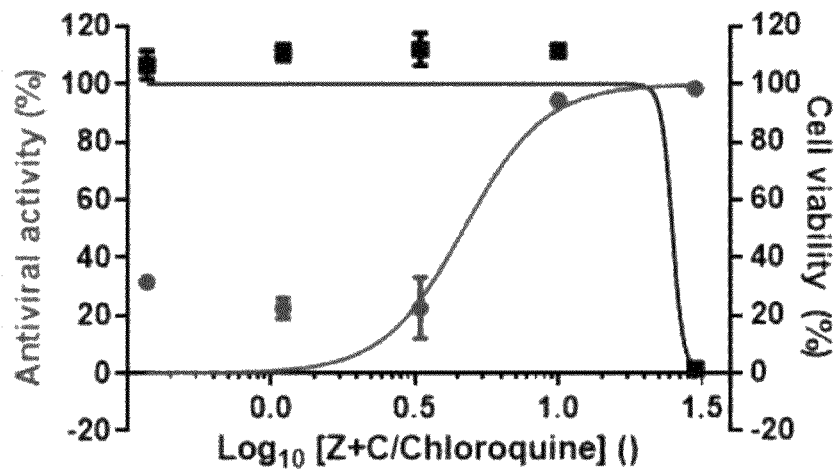
Figure 17:
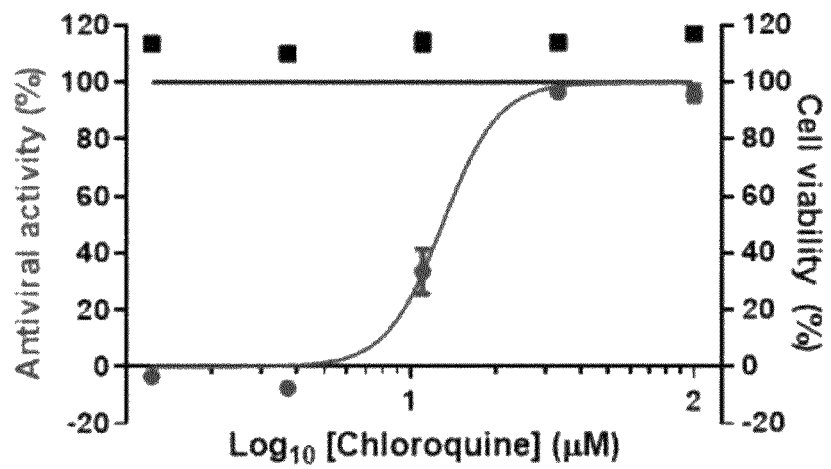

As shown in FIG. 8, CHP Hydrate (Pattern 2) was weighed in a glass vial and placed inside a vacuum oven set to 50° C. for 1 hour. XRPD analysis (top graph) showed that the material was still predominately Pattern 2 with some Pattern 1 peaks. As shown in FIG. 8, the input material from FIG. 5 (top graph) was returned to the oven, in which the temperature was increased to 80° C. The vial was placed inside the oven for an additional 18 hours. XRPD analysis (bottom graph) showed that the material was a mixture of Pattern 1 and 2. There was an extra peak at 8° 2θ that had not been previously seen in any pattern. As shown in FIG. 9, the Pattern 2 from FIG. 5 was dried for three different time periods, and the results were analyzed by XRPD. Drying the sample at 50° C. for 1 hour produced Pattern 2 with Pattern 1 peaks (to graph), drying the sample at 50° C. for 90 minutes also produced Pattern 2 with Pattern 1 peaks (third graph from the top), and drying the sample at 80° C. for 18 hours showed a mixture of Pattern 1 and Pattern 2 (bottom graph; see also the bottom graph of FIG. 6).

Biological Example 1

Antiviral activity and cytoprotection from SARS-CoV-2 viral infection were performed as follows.

Test Compounds/Compositions

The following compounds/compositions at various concentrations were used.

a) Zn: 600 μmol, 200 μmol, 67 μmol, 22 μmol, and 7.4 μmol
b) CHP: 30 mmol, 10 mmol, 3.3 mmol, 1.1 mmol, and 0.37 mmol
c) Zn+CHP: 600 μmol+30 mmol, 200 μmol+10 mmol, 67 μmol+3.3 mmol, 22 μmol+1.1 mmol, and 7.4 μmol+ 0.37 mmol,
d) Zn+CHP+chloroquine: 600 μmol+30 mmol+20 μmol, 200 μmol+10 mmol+20 20 μmol, 67 μmol+3.3 mmol+ 20 μmol, 22 μmol+1.1 mmol+20 μmol, and 7.4 μmol+ 0.37 mmol+20 μmol,
e) Chloroquine: 100 μmol, 33 μmol, 11 μmol, 3.7 μmol, and 1.2 μmol.

SARS-CoV-2 Cytoprotection Assay

The SARS-CoV-2 Cytoprotection assay employed Vero cells and SARS-CoV-2 strain. Virus and cells were mixed in the presence of test compound at various concentrations and incubated for 48 hours. The virus was pre-titered such that control wells exhibit 85 to 95% loss of cell viability due to virus replication. Therefore, antiviral effect or cytoprotection was observed when compounds prevent virus replication. Each assay plate contained cell control wells (cells only), virus control wells (cells plus virus), compound toxicity control wells (cells plus compound only), compound colorimetric control wells (compound only), as well as experimental wells (compound plus cells plus virus). Cytoprotection and compound cytotoxicity were assessed using dye reduction. The % reduction in viral cytopathic effects (CPE) was determined.

Cell Preparation

Vero cells (Kidney, African green monkey, *Cercopithecus aethiops*) were obtained from a depository (e.g., the American Type Culture Collection (ATCC, Rockville, Md., ATCC deposit no. CCL-81) and were grown in Dulbecco's Modified Eagle's Medium (DMEM) supplemented with 10% fetal bovine serum (FBS), 2.0 mM L-glutamine, 100 units/ml penicillin and 100 μg/ml streptomycin ("growth medium"). Cells were sub-cultured twice a week at a split ratio of 1:10 using standard cell culture techniques. Total cell number and percent viability determinations were performed using a hemacytometer and trypan blue exclusion. Cell viability must be greater than 95% for the cells to be utilized in the assay. The cells were seeded in 96-well tissue culture plates the day before the assay at a concentration of $1 \times 10^4$ cells/well.

MTS Staining for Cell Viability

At assay termination (48 hours post-infection), the assay plates were stained with the soluble tetrazolium-based dye MTS (3-(4,5-dimethylthiazol-2-yl)-5-(3carboxymethoxyphenyl)-2-(4-sulfophenyl)-2H-tetrazolium; CELLTITER® 96 Reagent, Promega) to determine cell viability and quantify compound toxicity.

MTS is metabolized by the mitochondrial enzymes of metabolically active cells to yield a soluble formazan product, allowing the rapid quantitative analysis of cell viability and compound cytotoxicity. This reagent was a stable, single solution that did not require preparation before use. At termination of the assay, 20-25 pL of MTS reagent was added per well and the microtiter plates were then incubated for 4-6 hrs at 37° C., 5% $CO_2$ to assess cell viability. Adhesive plate sealers were used in place of the lids, the sealed plate was inverted several times to mix the soluble formazan product and the plate was read spectrophotometrically at 490/650 nm with a Molecular Devices Vmax or SpectraMax Plus plate reader.

Evaluation of Antiviral Activities of the Compounds/Compositions

All the infection experiments were performed in a biosafety level-3 (BLS-3) laboratory. Five-point dose-response curves were generated for each drug. Vero cells were seeded at $2.0 \times 10^4$ cells per well in DMEM, supplemented with 10% FBS and 1× Antibiotic-Antimycotic solution (Gibco) in 24-well plate, 24 h prior to the experiment. For viral infection, SARS-CoV-2 was added at a multiplicity of infection (MOI) of 0.1. The cells were fixed at 24 hpi with 4% PFA and analyzed by immunofluorescence. The acquired images were analyzed to quantify cell numbers and infection ratios, and antiviral activity was normalized to positive (mock) and negative controls in each assay plate.

$EC_{50}$ (concentration inhibiting virus replication by 50%) and $CC_{50}$ (concentration resulting in 50% cell death) and a calculated SI (selectivity index $CC_{50}/EC_{50}$) were provided in FIGS. 13-17 and Table 1. In FIGS. 13-17, -■- represents cell viability (%) and -●- represents antiviral activity (%, relative amount of SRAR-CoV-2 S protein of which replication was inhibited by the tested compound/composition).

TABLE 1

| Tested compounds/compositions | Cytotoxicity ($CC_{50}$) | Effective drug concentration($EC_{50}$) | Selectivity index (SI) $CC_{50}/EC_{50}$ |
|---|---|---|---|
| (a) Zn | 486 µM | 480 µM | 1 |
| (b) CHP | 30 mM or higher | 19.6 mM | 1.6 or higher |
| (c) Zn + CHP | 24.7 mM | 3.3 mM | 7.5 |
| (d) Zn + CHP + chloroquinone | 24.9 mM | 4.7 mM | 5.3 |
| (e) chloroquinone | >100 µM | 13.0 µM | 7.7 |

As results, to surprise of the inventors, Zn, which was previous reported to have antiviral activity, kills the cells at the concentration of 600 µmol, and, when used alone, does not show any antiviral activity at concentrations 200 µmol or lower. On the other hand, CHP, when used alone, shows an antiviral activity at the concentration of 30 mmol, but does not show antiviral activity at a concentration of 10 µmol or lower.

However, Zn+CHP at At the 200 µmol+10 mmol and 67 µmol+3.3 mmol concentrations showed surprisingly high antiviral activity. At the 200 µmol+10 mmol and 67 µmol+3.3 mmol concentrations, 100% or almost 100% of the vero cells were survived. The effects were equivalent to remdesivir and were better than chloroquine, which were used as positive controls.

Chloroquine, which is known to increase the Zn influx into the cell, shows an increase of Zn penetration into the cells. However, the combination of Zn and chloroquine does not show any antiviral activity at equivalent concentrations to those of Zn+CHP.

Lung Protection Assessment in a Hamster Model of SARS-CoV-2 Infection

Syrian hamster study was carried out according to the procedures approved by the Institutional Animal Care and Use Committee of Chungbuk National University and complied with all relevant ethical regulations regarding animal research. In in vivo experiments, specific pathogen-free (SPF) animals were used in the Animal Biosafety Level 3 (ABSL-3) facilities for experiments with infectious virus.

Female Syrian hamsters, aged 8-10 weeks old, were obtained from Janvier Labs, France, were challenged with $1 \times 10^{4.5}$ TCID50/ml of SARS-CoV-2(NMC-nCoV02) via the intranasal route.

Vehicle and 1000 mg/kg Cyclo-Z were administered via an oral route daily 72 h before virus inoculation. At 3 dpi, tissue pathology of infected hamsters was examined by haematoxylin and eosin (H&E) staining in accordance with the established protocol.

The results are shown in FIGS. 9-12.

Biological Example 2

Anti-viral activity and cytotoxic activities are measured by following the same or modified procedure of Biological Example 1, except for employing the following test compositions:

CHP 5 mg+Zn 10 mg+remdesivir 0.75 mg–15 mg.

The specific pharmacological and biochemical responses observed in the assays described may vary according to and depending on the particular active compound selected or whether there are present pharmaceutical carriers, as well as type of formulation and mode of administration employed, and such expected variations or differences in the results are contemplated in accordance with practice of the present invention.

What is claimed is:

1. A method for treating viral infection in a subject in need thereof, comprising administering an effective amount of combination of a zinc and a cyclo(His-Pro) (CHP) to the subject;
   wherein the viral infection is caused by SARS-CoV-2.

2. The method of claim 1, wherein the cyclo(His-Pro) is anhydrous cyclo(His-Pro), amorphous cyclo(His-Pro), crystalline cyclo(His-Pro) hydrate, amorphous cyclo(His-Pro) hydrate, or a mixture thereof.

3. The method of claim 2, wherein the crystalline cyclo(His-Pro) hydrate is a crystalline cyclo(His-Pro) monohydrate.

4. The method of claim 3, the crystalline cyclo(His-Pro) hydrate is characterized by an X-ray powder diffraction (XRPD) diffractogram comprising peaks at 2θ values of 13.7°±0.2°, 17°±0.2°, and 27.3°±0.2°.

5. The method of claim 4, wherein the XRPD diffractogram further comprises a peak at 2θ value of 10°±0.2°.

6. The method of claim 4, wherein the XRPD is substantially similar to (b) of FIG. 2.

7. The method of claim 1, which further comprises administering a steroid.

8. The method of claim 1, wherein the zinc is a zinc salt selected from the group consisting of zinc chloride, zinc acetate, zinc gluconate, zinc stearate, zinc sulfate, zinc oxide, zinc picolinate, zinc orotate, and zinc citrate.

9. The method of claim 1, further comprising administering an additional anti-viral agent.

10. The method of claim 1, wherein a weight ratio of the zinc and the CHP is from about 1:100 to about 100:0.5, determined as zinc cation weight and as anhydrous CHP; or
    wherein the zinc is administered to the subject in an amount from about 0.01 to about 100 mg/kg/day, or
    wherein the CHP is administered to the subject in an amount from about 0.005 to about 1.5 mg/kg/day.

11. The method of claim 9, wherein the anti-viral agent is remdesivir.

12. The method of claim 1, wherein a weight ratio of the zinc and the CRP is from about 1:30 to about 10:0.5, determined as zinc cation weight and as anhydrous CRP;
  wherein a dose of the zinc is selected from the group consisting of about 0.01 to about 0.4 mg/kg/day, about 0.1 to about 2 mg/kg/day, about 2 to about 4 mg/kg/day, about 3 to about 8 mg/kg/day, about 1 to about 10 mg/kg/day, about 4 to about 7 mg/kg/day, about 7 to about 10 mg/kg/day, about 0.01 to about 0.18 mg/kg/day, about 0.5 to about 2 mg/kg/day, and about 1 to about 1.5 mg/kg/day, and
  wherein a dose of the CHP is selected from the group consisting of 0.005 to about 1.5 mg/kg/day, about 0.05 to about 15 mg/kg/day, about 0.05 to about 10 mg/kg/day, about 0.05 to about 5 mg/kg/day, about 0.01 to about 2 mg/kg/day, 0.1 to about 5 mg/kg/day, about 1 to about 15 mg/kg/day, about 1 to about 10 mg/kg/day, about 2 to about 7 mg/kg/day, about 3 to about 5 mg/kg/day, about 7 to about 10 mg/kg/day, about 0.5 to about 2 mg/kg/day, about 0.2 to about 4 mg/kg/day, about 0.8 to about 3 mg/kg/day, and about 1 to about 6 mg/kg/day.

13. A method for preventing and/or treating virally induced conditions in a subject in need thereof, comprising administering an effective amount of combination of a zinc and a cyclo(His-Pro) to the subject;
  wherein the virally induced conditions are caused by SARS-CoV-2.

14. The method of claim 13, wherein the cyclo(His-Pro) is anhydrous cyclo(His-Pro), amorphous cyclo(His-Pro), crystalline cyclo(His-Pro) hydrate, amorphous cyclo(His-Pro) hydrate, or a mixture thereof.

15. The method of claim 14, the crystalline cyclo(His-Pro) hydrate is characterized by an X-ray powder diffraction (XRPD) diffractogram comprising peaks at 2θ values of 13.7°±0.2°, 17°±0.2°, and 27.3°±0.2°.

16. The method of claim 15, wherein the XRPD is substantially similar to (b) of FIG. 2.

17. The method of claim 13, which further comprises administering a steroid; and/or further comprises administering an additional anti-viral agent.

18. The method of claim 13, wherein a weight ratio of the zinc and the CHP is from about 1:100 to about 100:0.5, determined as zinc cation weight and as anhydrous CHP;
  wherein a dose of the zinc is selected from the group consisting of about 0.01 to about 0.4 mg/kg/day, about 0.1 to about 2 mg/kg/day, about 2 to about 4 mg/kg/day, about 3 to about 8 mg/kg/day, about 1 to about 10 mg/kg/day, about 4 to about 7 mg/kg/day, about 7 to about 10 mg/kg/day, about 0.01 to about 0.18 mg/kg/day, about 0.5 to about 2 mg/kg/day, and about 1 to about 1.5 mg/kg/day, and
  wherein a dose of the CHP is selected from the group consisting of 0.005 to about 1.5 mg/kg/day, about 0.05 to about 15 mg/kg/day, about 0.05 to about 10 mg/kg/day, about 0.05 to about 5 mg/kg/day, about 0.01 to about 2 mg/kg/day, 0.1 to about 5 mg/kg/day, about 1 to about 15 mg/kg/day, about 1 to about 10 mg/kg/day, about 2 to about 7 mg/kg/day, about 3 to about 5 mg/kg/day, about 7 to about 10 mg/kg/day, about 0.5 to about 2 mg/kg/day, about 0.2 to about 4 mg/kg/day, about 0.8 to about 3 mg/kg/day, and about 1 to about 6 mg/kg/day.

19. The method of claim 13, wherein the zinc is a zinc salt selected from the group consisting of zinc chloride, zinc acetate, zinc gluconate, zinc stearate, zinc sulfate, zinc oxide, zinc picolinate, zinc orotate, and zinc citrate.

20. The method of claim 13, wherein the anti-viral agent is remdesivir.

* * * * *